US008455507B2

(12) United States Patent
Studley et al.

(10) Patent No.: US 8,455,507 B2
(45) Date of Patent: Jun. 4, 2013

(54) AMINOPYRIMIDINES USEFUL AS KINASE INHIBITORS

(75) Inventors: John Studley, Oxford (GB); Stephen Young, Oxford (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 723 days.

(21) Appl. No.: 12/595,703

(22) Filed: Oct. 13, 2009

(65) Prior Publication Data
US 2012/0095014 A1    Apr. 19, 2012

Related U.S. Application Data

(63) Continuation of application No. PCT/US2008/059975, filed on Apr. 11, 2008.

(60) Provisional application No. 60/923,495, filed on Apr. 13, 2007, provisional application No. 60/946,776, filed on Jun. 28, 2007.

(51) Int. Cl.
*C07D 403/14* (2006.01)
*A61K 31/4155* (2006.01)

(52) U.S. Cl.
USPC .......................................... 514/274; 544/317

(58) Field of Classification Search
USPC ......................................... 514/274; 544/317
See application file for complete search history.

(56) References Cited

U.S. PATENT DOCUMENTS

| | | | |
|---|---|---|---|
| 3,133,081 A | 5/1964 | Lafferty | |
| 3,755,322 A | 8/1973 | Winter et al. | |
| 3,935,183 A | 1/1976 | Baron et al. | |
| 3,998,951 A | 12/1976 | Harnish et al. | |
| 4,051,252 A | 9/1977 | Mayer et al. | |
| 4,493,726 A | 1/1985 | Burdeska et al. | |
| 4,540,698 A | 9/1985 | Ishikawa et al. | |
| 4,711,951 A | 12/1987 | Axen et al. | |
| 5,124,441 A | 6/1992 | Carlsson et al. | |
| 5,710,158 A | 1/1998 | Myers et al. | |
| 5,916,908 A | 6/1999 | Giese et al. | |
| 5,972,946 A | 10/1999 | Murata et al. | |
| 6,093,716 A | 7/2000 | Davis et al. | |
| 6,184,226 B1 | 2/2001 | Chakravarty et al. | |
| 6,200,977 B1 | 3/2001 | Cushing et al. | |
| 6,277,989 B1 | 8/2001 | Chakravarty et al. | |
| 6,495,582 B1 | 12/2002 | Hale et al. | |
| 6,528,509 B1 | 3/2003 | Hale et al. | |
| 6,528,513 B2 | 3/2003 | Cushing et al. | |
| 6,558,657 B1 | 5/2003 | Mandeville, III et al. | |
| 6,562,971 B2 | 5/2003 | Frauenkron et al. | |
| 6,579,983 B1 | 6/2003 | Batchelor et al. | |
| 6,589,958 B1 | 7/2003 | Frietze | |
| 6,593,326 B1 | 7/2003 | Bradbury et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,642,227 B2 | 11/2003 | Cao et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,689,778 B2 | 2/2004 | Bemis et al. | |
| 6,696,452 B2 | 2/2004 | Davies et al. | |
| 6,727,251 B2 | 4/2004 | Bebbington et al. | |
| 6,743,791 B2 | 6/2004 | Cao et al. | |
| 6,825,190 B2 | 11/2004 | Moon et al. | |
| 6,838,464 B2 | 1/2005 | Pease et al. | |
| 6,841,579 B1 | 1/2005 | Plowman et al. | |
| 6,846,928 B2 | 1/2005 | Bebbington et al. | |
| 6,884,804 B2 | 4/2005 | Choon-Moon | |
| 6,949,544 B2 | 9/2005 | Bethiel et al. | |
| 6,989,385 B2 | 1/2006 | Bebbington et al. | |
| 7,008,948 B2 | 3/2006 | Bebbington et al. | |
| 7,084,159 B2 | 8/2006 | Cao et al. | |
| 7,087,603 B2 | 8/2006 | Bebbington et al. | |
| 7,091,343 B2 | 8/2006 | Bebbington et al. | |
| 7,098,330 B2 | 8/2006 | Bebbington et al. | |
| 7,115,739 B2 | 10/2006 | Bebbington et al. | |
| 7,179,826 B2 | 2/2007 | Bebbington et al. | |
| 7,253,187 B2 | 8/2007 | Cao et al. | |
| 7,304,061 B2 | 12/2007 | Hale et al. | |
| 7,345,054 B2 | 3/2008 | Hale et al. | |
| 7,361,665 B2 | 4/2008 | Ledeboer et al. | |
| 7,390,815 B2 | 6/2008 | Davies et al. | |
| 7,427,681 B2 | 9/2008 | Bebbington et al. | |
| 7,473,691 B2 | 1/2009 | Davies et al. | |
| 7,491,730 B2 | 2/2009 | Forster et al. | |
| 7,528,142 B2 | 5/2009 | Binch et al. | |
| 7,531,536 B2 | 5/2009 | Bebbington et al. | |
| 7,557,106 B2 | 7/2009 | Charrier et al. | |
| 7,579,349 B2 | 8/2009 | Nowak et al. | |
| 7,625,913 B2 | 12/2009 | Bebbington et al. | |
| 7,691,853 B2 | 4/2010 | Bebbington et al. | |
| 7,737,151 B2 | 6/2010 | Mortimore et al. | |
| 7,767,672 B2 | 8/2010 | Binch et al. | |
| 7,820,685 B2 | 10/2010 | Binch et al. | |

(Continued)

FOREIGN PATENT DOCUMENTS

DE    2458965    6/1976
EP    0019811    12/1980

(Continued)

OTHER PUBLICATIONS

Jambhekar, S.S., "Biopharmaceutical Properties of Drug Substances" in Principles of Medicinal Chemistry, 4th ed., 12-24, (1995).

(Continued)

*Primary Examiner* — Jeffrey S. Lundgren
*Assistant Examiner* — Michael Schmitt
(74) *Attorney, Agent, or Firm* — Rory C. Stewart

(57) ABSTRACT

The present invention relates to compounds useful as inhibitors of Aurora protein kinases. The invention also provides pharmaceutically acceptable compositions comprising those compounds and methods of using the compounds and compositions in the treatment of various disease, conditions, and disorders. The invention also provides processes for preparing compounds of the invention.

23 Claims, No Drawings

U.S. PATENT DOCUMENTS

| | | |
|---|---|---|
| 7,863,282 B2 | 1/2011 | Bebbington et al. |
| 7,872,129 B2 | 1/2011 | Forster et al. |
| 7,951,820 B2 | 5/2011 | Bebbington et al. |
| 7,982,037 B2 | 7/2011 | Bebbington et al. |
| 7,989,456 B2 | 8/2011 | Mortimore et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0026664 A1 | 2/2003 | Mongrain |
| 2003/0036543 A1 | 2/2003 | Bebbington et al. |
| 2003/0055044 A1 | 3/2003 | Davies et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0069239 A1 | 4/2003 | Cai et al. |
| 2003/0069248 A1 | 4/2003 | Chakravarty et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington et al. |
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0049032 A1* | 3/2004 | Charrier et al. .......... 544/60 |
| 2004/0097501 A1 | 5/2004 | Bebbington et al. |
| 2004/0097531 A1 | 5/2004 | Ledeboer et al. |
| 2004/0157893 A1 | 8/2004 | Bebbington et al. |
| 2004/0214814 A1 | 10/2004 | Bebbington et al. |
| 2004/0229875 A1 | 11/2004 | Cao et al. |
| 2005/0004110 A1 | 1/2005 | Bebbington et al. |
| 2005/0038023 A1 | 2/2005 | Bebbington et al. |
| 2005/0049246 A1 | 3/2005 | Bemis et al. |
| 2005/0228005 A1 | 10/2005 | Moon et al. |
| 2005/0234059 A1 | 10/2005 | Hale et al. |
| 2006/0270660 A1 | 11/2006 | Charrier et al. |
| 2007/0179125 A1 | 8/2007 | Fraysse et al. |
| 2007/0190634 A1 | 8/2007 | Bebbington et al. |
| 2007/0265263 A1 | 11/2007 | Cao et al. |
| 2008/0287444 A1 | 11/2008 | Bebbington et al. |
| 2009/0181938 A1 | 7/2009 | Binch et al. |
| 2009/0221602 A1 | 9/2009 | Charrier et al. |
| 2010/0022502 A1 | 1/2010 | Jimenez et al. |
| 2010/0022507 A1 | 1/2010 | Jimenez et al. |
| 2010/0137305 A1 | 6/2010 | Binch et al. |
| 2010/0215772 A1 | 8/2010 | Mortimore et al. |
| 2010/0267628 A1 | 10/2010 | O'Harte et al. |
| 2010/0310675 A1 | 12/2010 | Binch et al. |
| 2010/0317641 A1 | 12/2010 | Mortimore et al. |
| 2011/0020376 A1 | 1/2011 | Jimenez et al. |
| 2011/0020377 A1 | 1/2011 | Pierce et al. |
| 2011/0020469 A1 | 1/2011 | Binch et al. |
| 2011/0021559 A1 | 1/2011 | Jimenez et al. |
| 2011/0046104 A1 | 2/2011 | Mortimore et al. |
| 2011/0060013 A1 | 3/2011 | Mortimore et al. |
| 2011/0086856 A1 | 4/2011 | Bebbington et al. |
| 2011/0269732 A1 | 11/2011 | Golec et al. |

FOREIGN PATENT DOCUMENTS

| | | |
|---|---|---|
| EP | 136976 | 4/1985 |
| EP | 0302312 | 2/1989 |
| GB | 2052487 | 1/1981 |
| JP | 10-130150 | 5/1998 |
| JP | 2000-026421 | 1/2000 |
| JP | 06-65237 | 10/2007 |
| WO | 9208715 | 5/1992 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0039101 | 6/2000 |
| WO | 0038675 | 7/2000 |
| WO | 0042029 | 7/2000 |
| WO | 0059509 | 10/2000 |
| WO | 0078757 | 12/2000 |
| WO | 0112621 | 2/2001 |
| WO | 0139777 | 6/2001 |
| WO | 0140215 | 6/2001 |
| WO | 0144242 | 6/2001 |
| WO | 0147879 | 7/2001 |
| WO | 0160816 | 8/2001 |
| WO | 0164655 | 9/2001 |
| WO | 0179198 | 10/2001 |
| WO | 0174768 | 11/2001 |
| WO | 0125220 | 12/2001 |
| WO | 0208244 | 1/2002 |
| WO | 0218346 | 3/2002 |
| WO | 0222601 | 3/2002 |
| WO | 0222602 | 3/2002 |
| WO | 0224667 | 3/2002 |
| WO | 0247690 | 6/2002 |
| WO | 0250065 | 6/2002 |
| WO | 0250066 | 6/2002 |
| WO | WO 0250065 A2 * | 6/2002 |
| WO | 02079197 | 10/2002 |
| WO | 03077921 | 9/2003 |
| WO | 03078426 | 9/2003 |
| WO | 03078427 | 9/2003 |
| WO | 04000833 | 12/2003 |
| WO | 2004013140 | 2/2004 |
| WO | 2004037814 | 5/2004 |
| WO | 2007023382 | 1/2007 |
| WO | 2007041358 | 4/2007 |
| WO | 2007059299 | 5/2007 |
| WO | 2008057940 | 5/2008 |
| WO | WO2008077086 | 6/2008 |

OTHER PUBLICATIONS

Layzer, R.B., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med . Chem., 38 (18): 3547-3557 (1995).

Medwid, J.B. et al., "Preparation of Triazolo[ 1,5-c]pyrimidines as Potential Antiasthma Agents," J. Med. Chem. 33, 1230-1241 (1990).

Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).

Cohen, P., "Dissection of the Protein Phosphorylation Cascades Involved in Insulin and Growth Factor Action", Biochem. Soc. Trans., 21, 555-567 (1993).

Haq, S. et al., "Glycogen Synthase Kinase-3β Is a Negative Regulator of Cardiomyocyte Hypertrophy", J. Cell Biol., 151(1), 117-129 (2000).
Fischer, P.M. et al., "Inhibitors of Cyclin-Dependent Kinases as Anti-Cancer Therapeutics", Current Med. Chem., 7, 1213-1245 (2000).
Mani, S. et al., "Cyclin-dependent kinase: novel anticancer agents", Exp. Opin. Invest. Drugs., 8, 1849-1870 (2000).
Fry, D.W. et al., "Inhibitors of cyclin-dependent kinases as therapeutic agents for the treatment of cancer", Current Opin. Oncol. Endoc. & Metab. Investig., 2-40-59 (2000).
Bokemeyer, D. et al., "Multiple intracellular MAP kinase signaling cascades", Kidney Int., 49, 1187-1198 (1996).
Anderson, N.G. et al., "Multiple intracellular MAP kinase signaling cascades", Nature, 343, 651-653 (1990).
Crews, C.M. et al., "The Primary Structure of MEK, a Protein Kinase That Phosphorylates the ERK Gene Product", Science, 258, 478-480 (1992).
Bjorbaek, C. et al, "Divergent Functional Roles for p90rsk Kinase Domains", J. Biol. Chem., 270(32), 18848-18552 (1995).
Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).
Raingeaud, J. et al., MMK3- and MMK6-Regulated Gene Expression Is Mediated by p38 Mitogen-Activated Protein Kinase Signal Transduction Pathway, Mol. Cell. Biol., 16, 1247-1255 (1996).
Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).
Moodie, S.A. et al., "Complexes of Ras-GTP with Raf-1 and Mitogen-Activated Protein Kinase Kinase", Science, 260 (5114), 1658-1661 (1993).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).
Sivaraman, V.S., et al., "Hyperexpression of Mitogen-activated Protein Kinase in Human Breast Cancer", J. Clin. Invest., 99(7), 1478-1483 (1997).
Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).
Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).
Kazuhiko, N. et al., "Akt/Protein Kinase B Prevents Injury-Induced Motoneuron Death and Accelerates Axonal Regeneration", J. of Neuroscience, 20(8), 2875-2986 (2000).
Molina, T.J. et al., "Profound block in thymocyte development in mice lacking p56lck", Nature, 357, 161-164 (1992).
Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).
Douglas, G. et al., "Introduction to viral diseases", Cecil Textbook of Medicine, 20th Edition, vol. 2, p. 1739-1747.
Salomon, S. et al., "Cancer Chemotherapy", Lange Medical Book, Basic and Clinical Pharmacology, 7th edition, 55, p. 881-884.
Torryiabe, K. et al., "Preparation of self-conaining arylthiazoles and insecticides", Chemical abstracts, [ Columbus, Ohio.
IUPAC Compendium of Chemical Terminology on a definition of "aliphatic compounds" found from http://www.chemsoc.org/chembytes/goldbook/index.htm (last visited on Nov. 18, 2007).
The International Search Report received in the corresponding PCT Application No. PCT/US2008/059975.
Alonso, M. et al., "GSK-3 Inhibitors: Discoveries and Developments", Current Medicinal Chemistry, 11, 755-763 (2004).
Anonymous, "Vertex Inhbitors of Aurora-2, glycogen synthase kinase-3 and Src Kinase", Expert Opin. Ther. Patents, 14(3): 439-443 (2004).
Baig, G.U. et al., "Triazines and Related Products. Part 28' Conversion of 3-Aryl-I-(2-cyanopheny1) triazines into 3-Arylqu i nazol i n-4(3H)-ones with Formamide" J. Chem. Soc. Perkin Trans. I, 3765-2766 (1984).

Bischoff, J.R., et al., "A homologue of *Drosophila aurora* kinase is oncogenic and amplified in human colorectal cancers", The EMBO Journal, 17(11): 3052-3065 (1998).
Bischoff, J.R., et al., "The Aurora/Ipl1p kinase family: regulators of chromosome segregation and cytokinesis", Cell Biology, 9, 454-459 (1999).
Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).
Wolff, M.E., "Burger's Medicinal Chemistry and Drug Discovery," 5th ed., vol. 1: Principles and Practice, 975-977 (1995).
Cohen, P. et al., "The renaissance of GSK3," Nat. Rev. Mol. Biol., 2, 769-776 (2001).
Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).
Harrington, E.A. et al., "VX-680, a potent and selective small-molecule inhibitor of the Aurora kinases, suppresses tumor growth in vivo," Nat. Med., 10(3): 262-267 (2004).
Heutink, P., "Untangling tau-related dementia", Hum. Mol. Genet., 9(6): 979-986 (2000).
Nigg, E.A., "Mitotic Kinases as Regulators of Cell Division and its Checkpoints," Nat. Rev. Mol. Cell Biol., 2: 21-32 (2001).
Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).
Nakajima, Y. et al., "Pyrazoles agricultural and horticultural bactericides," CAPLUS listing Accession No. 1994:292136, JP 06065237 (1994).
Kelarev, V.I. et al., "Synthesis of amino derivatives of 1,3,5-triazine containing 1,3-4-thiadiazole fragments," DATABASECA "Online!" Chemical Abstract Service, Columbus, OH, US; Database Accession No. 1998:69514 XP002242653 abstract & Izvestiya Vysshikh Uchebnkh Zavedenii, Khimiya I Khimicheskaya Tekhnologiya, 40(5): 27-32 (1997).
Chalmers, D.T. et al., "Corticotrophin-releasing factor receptors: from molecular biology to drug design," TiPS, 17, 769-776 (2001).
Kim, L. et al., "GSK3, a master switch regulating cell-fate specification and tumorigenesis," Current Opinion in Genetics & Development, 10:508-514 (2000).
Lyrer, P., Schweiz. Med. Woohen Schr., 124(45); 2005-2012 (1994).
Banker, G.S. et al., "Modern Pharmaceutics", 451 & 596, 3rd ed., Marcel Dekker, New York (1996).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Ivashchenko A. V. et al., "Synethsis and Study of Heteroaromatic Ligands Containing a Pyrimidine Ring", Khim. Geterotsikl. Soedin., (12), 1673-7, (1980) (in English).
Brownlees, J. et al., "Tau phosphorylation in transgenic mice expressing glycogen synthase kinase-3beta transgenes", Neuroreport., 8(15), 3251-5 (1997).
Biagi, G. et al., "Synthesis of 4,6 Disubstituted and 4,5,6-Trisubstituted-2-Phenyl-pyrimidines and Their Affinity Towards A1 Adenosine Receptors", Farmaco., 52(1), 61-65 (1997).
Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).
Zhang, Z. et al., "Destabilization of β catenin by mutations in presenilin-1 potentiates neuronal apoptosis", Nature, 395, 698-702 (1998).
Takashima, K. et al., "Tau Protein Kinase I is Essential for Amyloid β-Protein-Induced Neurotoxicity", PNAS 90, 7789-7793 (1993).
Pei, J. et al., "Distribution, Levels, and Activity of Glycogen Synthase Kinase-3 in the Alzheimer Disease Brain", J. Neuropathol. Exp., 56, 70-78 (1997).
Rueeger, H et al., "Design, synthesis and SAR of a series of 2-substituted 4-amino-quinazoline neuropeptide Y Y5 receptor antagonists", Bioorg. Med. Chem. Lett., 10(11), 1175-1180 (2000).
Glossary of Class Names of Organic Compounds and Reactive Intermediates Based on Structure found from http://www.chem.qmul.ac.uk/iupac/class/index.html (last visited on Nov. 18, 2007).

Nomenclature found from http://www.cem.msu.edu/~reusch/VirtualText/nomen1.htm (last visited on Nov. 18, 2007).

Coghlan, M.P. et al., "Selective small molecule inhibitors of glycogen synthase kinase-3 modulate glycogen metabolism and gene transcription", Chemistry & Biology, 7, 793-83 (2000).

Klein, P.S. et al., "A molecular mechanism for the effect of lithium on development", PNAS, 93: 8455-8459 (1996).

Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).

Massillon, D. et al., "Identification of the glycogenic compound 5-iodotubercidin as a general protein kinase inhibitor", Biochem J., 299: 123-128 (1994).

Fox T. et al., "A single amino acid substitution makes ERK2 susceptible to pyridinyl imidazole inhibitors of p38 MAP kinase", Protein Sci., 7: 2249-2255 (1998).

Takayanagi, H. et al., "Suppression of arthritic bone destruction by adenovirus-mediated csk gene transfer to synoviocytes and osteoclasts", J. Clin. Invest., 104, 137-146 (1999).

Boschelli et al., "Small molecule inhibitors of Src family kinases", Drugs of the Future, 25(7): 717-736 (2000).

Talamonti, M.S. et al., "Increase in activity and level of pp60c-src in progressive stages of human colorectal cancer", J Clin Invest., 91(1): 53-60 (1993).

Lutz, M.L. et al., "Overexpression and Activation of the Tyrosine Kinase Src in Human Pancreatic Carcimona", Biochem. Biophys. Res. 243, 503-508 (1998).

Rosen, N. et al., "Analysis of pp60c-src Protein Kinase Activity in Human Tumor Cell Lines and Tissues", J.Biol. Chem., 261, 13754-13759 (1986).

Bolen, J.B. et al., "Activation of pp60c-src protein kinase activity in human colon carcinoma", PNAS, 84, 2251-2255 (1987).

Masaki, T. et al., "pp60c-src Activation in Hepatocellular Carcinoma of Humans and LEC Rats", Hapatology, 27, 1257 (1998).

Biscardi, J.S. et al., "c-Src, Receptor Tyrosine Kinases, and Human Cancer", Adv. Cancer Res., 76, 61 (1999).

Lynch, S.A. et al., "Increased Expression of the src Proto-Oncogene in Hairy Cell Leukemia and a Subgroup of B-Cell Lymphomas", Leukemia, 7(9), 1416-1422 (1993).

Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).

Staley, C.A. et al., "Decreased Tumorigenicity of a Human Colon Adenocarcinoma Cell Line by an Antisense Expression Vector Specific for c-Src", Cell Growth Diff., 8, 269-274 (1997).

Singhal, N. et al., "Synthesis and Antimalarial Activity of Some New Quinazoline Derivatives", Indian Chem. Soc., 61, 690-693 (1984).

Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).

Namikowa et al., "Akt/Protein Kinase B Prevents Injury-Induced Motoneuron Death and Accelerates Axonal Regeneration", The Journal of Neuroscience, Apr. 15, 2000, 20(8):2875-2886.

Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).

Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).

Tanji, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).

Charpiot, B. et al., "Quinazolines: Combined type 3 and 4 phosphodiesterase inhibitors", Bioorg. Med. Chem. Lett. 8 (20), 2891-2896 (1998).

Shikhaliev, K.S. et al., "Heterocyclization of quinazol-2-ylguanidines. 1. Reaction with amino acids", Chem. Heterocycl. Compd., 35 (7), 818-820 (1999).

Singh, S.P. et al., "Synthesis & Mass Spectra of Some Substituted 2-(2'-Benzazolylamino)pyrimidines", Indian J. Chem. Sect. B, 22(1); 37-42 (1983).

Ti, J. et al., "Anticandidal activity of pyrimidine-peptide conjugates", J. Med. Chem., 23(8), 913-918 (1980).

Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).

Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).

Myers, M.R. et al., "The synthesis and SAR of new 4-(N-alkyl-N-phenyl)amino-6,7-dimethoxyquinazolines and 4-(N-alkyl-N-phenyl)aminopyrazolo[3,4-d]pyrimidines, inhibitors of CSF-1R tyrosine kinase activity", Bioorg. Med. Chem. Lett., 7, 4, 421-424 (1997).

Agarwal, N. et al., "Suitably functionalised pyrimidines as potential antimycotic agents", Bioorg. Med. Chem. Lett., 10, 8, 703-706 (2000).

Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Noell, C.W. et al., "Potential Purine Antagonists. XX. The Preparation and Reactions of Some Methylthiopurines", J. Am. Chem. Soc., 81(22), 5997-6007 (1959).

Lubbers, T. et al., "Design, synthesis, and structure—activity relationship studies of ATP analogues as DNA gyrase inhibitors", Bioorg. Med. Chem. Lett., 10, 8, 821-826 (2000).

D'Atri, G. et al., "Novel pyrimidine and 1,3,5-triazine hypolipemic agents", J. Med. Chem. 27(12), 1621-1629 (1984).

Venugopalan, B. et al., "Synthesis and antimalarial activity of pyrido[3,2-f)quinozalines and their oxides", Indian J. Chem. Sect. B, 34, 9, 778-790 (1995).

Curd, F.H.S. et al, "Synthetic antimalarials. Part XVII. Some aminoalkylaminoquinoline derivatives", J. Chem. Soc., 899-909 (1947).

Haworth, R.D. et al., "Synthetic antimalarials. Part XXVII. Some derivatives of phthalazine, quinoxaline, and isoquinoline", J. Chem. Soc., 777-782 (1948).

Nair, M.D., et al., "3-Chloroisocarbostyril & Its Chlorination Products", Indian J. Chem., 467-470 (1967).

Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Gnecco, D. et al., "An Improved Preparation of 1-Methyl-4-Cyano-4-phenylpiperidine", Org. Prep. Proced. Int., 18 (4), 478-480 (1996).

Fedorynski, M. et al., "Synthesis of 1-Arycyclopropanecarbonitriles under Phase-transfer Catalytic Conditions", Org. Prep. Proced. Int., 27(3), 355-359 (1995).

Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).

Prasad, G. et al., "18-Crown-6 as a catalyst in the dialkylation of o-nitrophenacyl derivatives", J. Org. Chem., 25, 7188-7190 (1991).

Moss, R.A. et al., "Conversion of 'Obstinate' Nitriles to Amidines by Garigipati's Reaction", Tetrahedron Lett., 36(48), 8761-8764 (1995).

Garigipati, R.S., "An efficient conversion of nitriles to amidines", Tetrahedron Lett., 31(14), 1969-1972 (1990).

Warner, S.L. et al, "Targeting Aurora-2 Kinase in Cancer," Mol. Cancer Thera., 2, 589-585, 2003.

Wagman, A.S. et all, "Discovery and Development of GSK3 Inhibitors for the Treatment of Type 2 Diabetes," Current Pharmaceutical Design, 10, 1105-1137 (2004).

Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).

Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).

Soriano, P. et al., "Targeted Disruption of the C-SIC Pmto-Oncogene Leads to Osteopetrosis in Mice," Cell, 64: 693-702, (1991).

Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).

Casanova, B. et al., "Revisión critica de la patogenia actual de la esclerosis múltiple y futuras direcciones posibles," Rev. Neurol., 28 (9): 909-915 (1999).

Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).

Simone, J.V., "Oncology: Introduction" in Cecil Textbook in Medicine, 20th ed., vol. 1, 1004-1010 (1996).

Coleman, R.A., "The Biological Evaluation of New Compounds" in Medicinal Chemistry: Principles and Practice, King, Frank D. ed, Royal Society of Chemistry, 53-66 (1994).

The Condensed Chemical Dictionary, Sixth Edition by Arthur and Elizabeth Rose, 38 (1961).

Damasio, A.R., "Alzheimer's Disease and Related Dementia," in Cecil Textbook of Medicine, 20th ed., 2: 1992-1996 (1996).

Rogers, E. et al., "The aurora kinase AIR-2 functions in the release of chromosome cohesion in Caenorhabditis elegans meiosis," J. Cell Biol., 157(2): 219-229 (2002).

Fisher A., "Therapeutic Strategies in Alzheimer's Disease: M1 Muscarinic Agonists," Jpn. J. Pharmacol., 84(2):101-12 (2000).

Frame, M.C., "Src in cancer: deregulation and consequences for cell behaviour," Biochimica et Biophysica Acta., 1602, 114-130 (2002).

Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).

Ganellin, C.R., "Past Approaches to Discovering New Drugs as Medicines" in Medicinal Chemistry, Principles and Practices. King, Frank D. ed, Royal Society of Chemistry, 189-205 (1994).

Hamdane, M. et al., "A Therapeutic Target in Alzheimer Neurodegeneration," J. Mol. Neurosci., 19(3): 275-87 (2002).

Hardt, S.E. et al., "Glycogen Synthase Kinase-3β—A Novel Regulator of Cardiac Hypertrophy and Development," Circulation Research, 90: 1055-1063 (2002).

Parnell, E.W., "2-Cyano-4-nitrophenylhydrazine and 3-Amino-5-nitroindazole", J. Chem. Soc., 2363-2365 (1959).

Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).

Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Okafor, C.O., "Studies in the Heterocyclic Series. X. 1,3,9-Triazaphenothiazine Ring System, a New Phenothiazine Ring," J. Org. Chem., 40(19): 2753-2755 (1975).

* cited by examiner

AMINOPYRIMIDINES USEFUL AS KINASE INHIBITORS

CROSS REFERENCE TO RELATED APPLICATIONS

This application is a continuation application of International Patent Application No. PCT/US2008/059975, filed on Apr. 11, 2008, which in turn claims the benefit under 35 U.S.C. §119, of U.S. Provisional patent application Nos. 60/923,495, filed Apr. 13, 2007 and 60/946,776, filed Jun. 28, 2007 entitled "AMINOPYRIMIDINES USEFUL AS KINASE INHIBITORS", and the entire contents of these applications are hereby incorporated by reference.

TECHNICAL FIELD OF THE INVENTION

The present invention relates to compounds useful as inhibitors of Aurora protein kinases. The invention also relates to pharmaceutically acceptable compositions comprising the compounds of the invention, methods of using the compounds and compositions in the treatment of various disorders, and processes for preparing the compounds.

BACKGROUND OF THE INVENTION

The Aurora proteins are a family of three related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas.

A number of studies have now demonstrated that depletion or inhibition of Aurora-A or -B in human cancer cell lines by siRNA, dominant negative antibodies or neutralizing antibodies disrupts progression through mitosis with accumulation of cells with 4N DNA, and in some cases this is followed by endoreduplication and cell death.

The Aurora kinases are attractive targets due to their association with numerous human cancers and the roles they play in the proliferation of these cancer cells. It would be desirable to have an Aurora kinase inhibitor with favorable drug-like properties, such as stability in human liver microsomes. Accordingly, there is a need for compounds that inhibit Aurora kinases and also exhibit favorable drug-like properties.

SUMMARY OF THE INVENTION

This invention provides compounds and pharmaceutically acceptable compositions thereof that are useful as inhibitors of Aurora protein kinases. More specifically, this invention provides compounds that are metabolically stable in human liver microsomes and/or potently inhibit cell proliferation.

These compounds are represented by formula I:

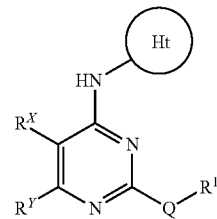

I or a pharmaceutically acceptable salt thereof, wherein the variables are as defined herein.

These compounds and pharmaceutically acceptable compositions thereof are useful for inhibiting kinases in vitro, in vivo, and ex vivo. Such uses include treating or preventing myeloproliferative disorders and proliferative disorders such as melanoma, myeloma, leukemia, lymphoma, neuroblastoma, and cancer. Other uses include the study of kinases in biological and pathological phenomena; the study of intracellular signal transduction pathways mediated by such kinases; and the comparative evaluation of new kinase inhibitors.

DETAILED DESCRIPTION OF THE INVENTION

One embodiment of this invention provides a compound of formula I:

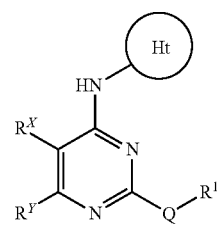

I or a pharmaceutically acceptable salt thereof, wherein:
Ht is

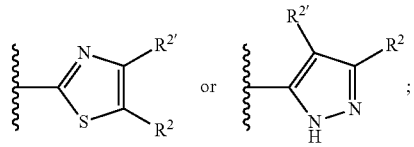

$R^2$ is H, $C_{1-3}$ alkyl, or cyclopropyl;
$R^{2'}$ is H;
Q is —O—, —S—, or —C(R')$_2$—;
$R^X$ is H or F;
$R^Y$ is

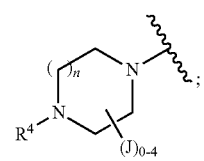

each J is independently F or $C_{1-6}$alkyl;
R' is H or $C_{1-3}$alkyl, or two R' taken together with the carbon atom to which they are attached, form a $C_{3-5}$ cycloalkyl;

n is 1 or 2;

$R^4$ is H, $C_{1-6}$alkyl, $C_{3-8}$ cycloaliphatic, or a 4-8 membered heterocyclyl containing 1-2 heteroatoms selected from O, N, or S; wherein said alkyl, cycloaliphatic or heterocyclyl is optionally and independently substituted with 0-6 occurrences of $C_{1-6}$alkyl, —O—($C_{1-6}$alkyl), $NH_2$, OH, =O, halo, CN, or $NO_2$;

$R^1$ is an 8-12 membered bicyclic heteroaryl ring containing 1-5 heteroatoms selected from O, N, and S and optionally substituted with 0-4 $J^D$; wherein each ring in said system contains 4-8 ring members and 1-4 heteroatoms selected from O, N, and S;

each $J^D$ is independently $C_{1-6}$alkyl, —O—($C_{1-6}$alkyl), halo, or oxo wherein each $C_{1-6}$alkyl is optionally substituted with 0-6 fluoro.

In some embodiments, Q is —S—.

In some embodiments, Ht is

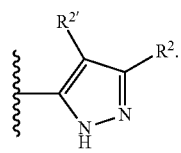

Alternatively, in another embodiment, Ht is

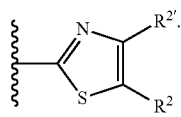

In other embodiments, $R^2$ is $C_{1-3}$ alkyl or cyclopropyl. In yet other embodiments, $R^{2'}$ is H.

In some embodiments, $R^X$ is H.

In some embodiments, n is 1. In other embodiments, n is 2.

In some embodiments, $R^4$ is H, $C_{1-6}$alkyl, $C_{3-8}$ cycloaliphatic, or a 4-8 membered heterocyclyl containing 1-2 heteroatoms selected from O or N. In other embodiments, $R^4$ is $C_{1-6}$alkyl, $C_{3-8}$ cycloaliphatic, or a 4-8 membered heterocyclyl containing 1-2 heteroatoms selected from O or N. In yet other embodiments, $R^4$ is H, $C_{2-6}$alkyl, $C_{3-8}$ cycloaliphatic, or a 4-8 membered heterocyclyl containing 1-2 heteroatoms selected from O or N. In some embodiments, $R^4$ is a 4-8 membered heterocyclyl containing 1-2 heteroatoms selected from O or N. In other embodiments, $R^4$ is a 5-6 membered heterocyclyl containing 1-2 heteroatoms selected from O or N. In some embodiments, $R^4$ is $C_{1-6}$alkyl. In other embodiments, $R^4$ is $C_{2-6}$alkyl. In some embodiments, $R^4$ is $C_{1-6}$haloalkyl. In other embodiments, $R^4$ is $C_{2-6}$haloalkyl. In yet other embodiments, $R^4$ is $C_{3-6}$ cycloalkyl. In some embodiments, $R^4$ is $C_{2-6}$haloalkyl, $C_{3-6}$cycloalkyl, or a 5-6 membered heterocyclyl containing 1-2 heteroatoms selected from O or N. In some embodiments, said heterocyclyl contains 1-2 nitrogen atoms.

In some embodiments, $R^4$ is optionally and independently substituted with 0-6 occurrences of $C_{1-6}$alkyl, —O—($C_{1-6}$alkyl), $NH_2$, OH, =O, halo, CN, or $NO_2$.

In another embodiment, $R^1$ is an 8-12 membered bicyclic heteroaryl containing 1-5 heteroatoms selected from O, N, and S and optionally substituted with 0-4 $J^D$.

In some embodiments, $R^1$ is a 6:6 ring system. A 6:6 ring system is a bicyclic fused ring system wherein each monocyclic ring within the ring system contains 6 ring atoms.

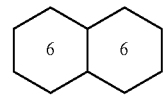

6:6 ring systems can be either saturated, partially unsaturated, or fully unsaturated (i.e. aromatic). Examples of 6:6 ring systems include, but are not limited to, quinoline, quinazoline, quinoxalines, pyridopyrimidine, and naphthyridine. In some embodiments, $R^1$ is quinoline.

In other embodiments, $R^1$ is a 6:5 ring system.

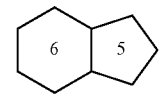

A 6:5 ring system is a bicyclic fused ring system wherein one monocyclic ring within the ring system contains 6 ring atoms, and the other monocyclic ring within the ring system contains 5 ring atoms.

6:5 ring systems can be either saturated, partially unsaturated, or fully unsaturated (i.e. aromatic). Examples of 6:5 ring systems include, but are not limited to, indole, indazole, benzimidazole, benzothiazole, pyrazolopyridine, imidazopyridine, pyrazolopyrimidine, imidazopyrimidine, and benzothiophene. In some embodiments, $R^1$ is a 6:5 ring system that contains 2 nitrogen atoms. In some embodiments, $R^1$ is a benzimidazole, indazole, or imidazopyridine ring. In some embodiments, $R^1$ is a benzimidazole ring.

Another embodiment of this invention provides a compound of formula I or a pharmaceutically acceptable salt thereof, wherein:

Ht is

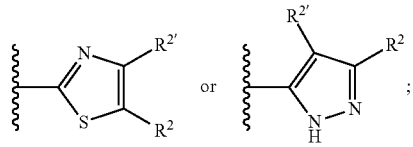

$R^2$ is H, $C_{1-3}$ alkyl, or cyclopropyl;
$R^{2'}$ is H;
Q is —O—, —S—, or —C(R')$_2$—;
$R^X$ is H or F;
$R^Y$ is

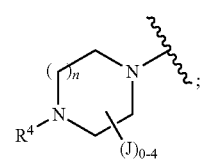

each J is independently F or $C_{1-6}$alkyl;
R' is H or $C_{1-3}$alkyl, or two R' taken together with the carbon atom to which they are attached, form a $C_{3-5}$ cycloalkyl;
n is 1 or 2;

R⁴ is H, $C_{1-6}$alkyl, $C_{3-8}$ cycloaliphatic, or a 4-8 membered heterocyclyl containing 1-2 heteroatoms selected from O, N, or S; wherein said alkyl, cycloaliphatic or heterocyclyl is optionally and independently substituted with 0-6 occurrences of $C_{1-6}$alkyl, —O—($C_{1-6}$alkyl), $NH_2$, OH, =O, halo, CN, or $NO_2$;

R¹ is an 8-12 membered bicyclic heteroaryl ring containing 1-5 heteroatoms selected from O, N, and S and optionally substituted with 0-4 $J^D$; and each $J^D$ is independently $C_{1-6}$alkyl, —O—($C_{1-6}$alkyl), halo, or oxo wherein each $C_{1-6}$alkyl is optionally substituted with 0-6 fluoro.

In some embodiments, Q is —S—.
In some embodiments, Ht is

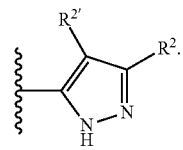

Alternatively, in another embodiment, Ht is

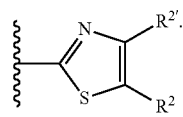

In other embodiments, $R^2$ is $C_{1-3}$ alkyl or cyclopropyl. In yet other embodiments, $R^{2'}$ is H.

In some embodiments, $R^X$ is H.

In some embodiments, n is 1. In other embodiments, n is 2.

In some embodiments, R⁴ is H, $C_{1-6}$alkyl, $C_{3-8}$ cycloaliphatic, or a 4-8 membered heterocyclyl containing 1-2 heteroatoms selected from O or N. In other embodiments, R⁴ is $C_{1-6}$alkyl, $C_{3-8}$ cycloaliphatic, or a 4-8 membered heterocyclyl containing 1-2 heteroatoms selected from O or N. In yet other embodiments, R⁴ is H, $C_{2-6}$alkyl, $C_{3-8}$ cycloaliphatic, or a 4-8 membered heterocyclyl containing 1-2 heteroatoms selected from O or N. In some embodiments, R⁴ is a 4-8 membered heterocyclyl containing 1-2 heteroatoms selected from O or N. In other embodiments, R⁴ is a 5-6 membered heterocyclyl containing 1-2 heteroatoms selected from O or N. In some embodiments, R⁴ is $C_{1-6}$alkyl. In other embodiments, R⁴ is $C_{2-6}$alkyl. In some embodiments, R⁴ is $C_{1-6}$haloalkyl. In other embodiments, R⁴ is $C_{2-6}$haloalkyl. In yet other embodiments, R⁴ is $C_{3-6}$ cycloalkyl. In some embodiments, R⁴ is $C_{2-6}$haloalkyl, $C_{3-6}$cycloalkyl, or a 5-6 membered heterocyclyl containing 1-2 heteroatoms selected from O or N. In some embodiments, said heterocyclyl contains 1-2 nitrogen atoms.

In some embodiments, R⁴ is optionally and independently substituted with 0-6 occurrences of $C_{1-6}$alkyl, —O—($C_{1-6}$alkyl), $NH_2$, OH, =O, halo, CN, or $NO_2$.

In another embodiment, R¹ is an 8-12 membered bicyclic heteroaryl containing 1-5 heteroatoms selected from O, N, and S and optionally substituted with 0-4 $J^D$.

In some embodiments, R¹ is a 6:6 ring system.
In other embodiments, R¹ is a 6:5 ring system.
In some embodiments, the variables of Formula I include those shown in Table 1 below.

Another embodiment provides compounds selected from the following:

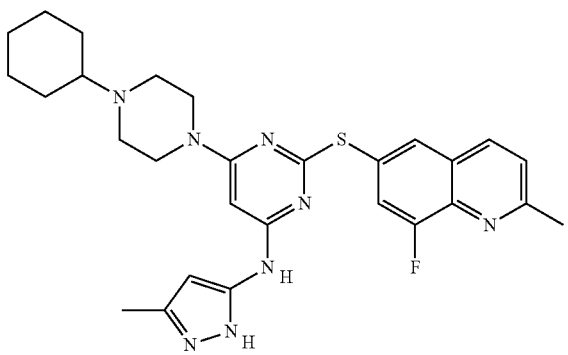

I-1

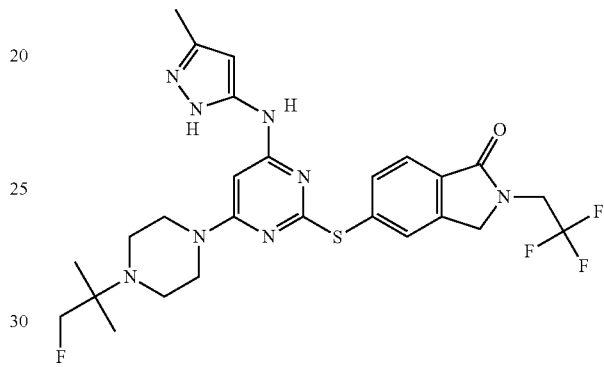

I-2

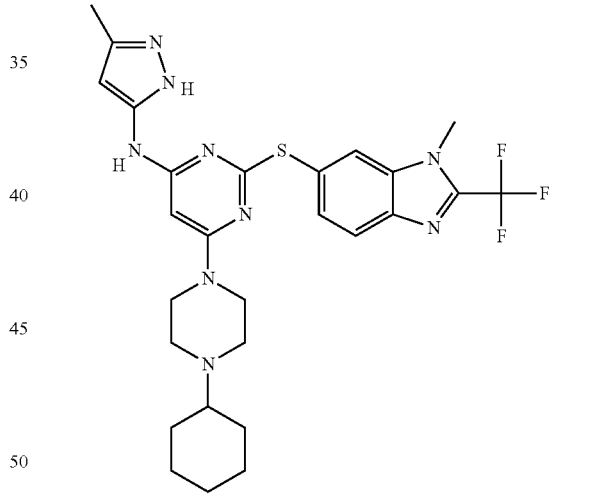

I-3

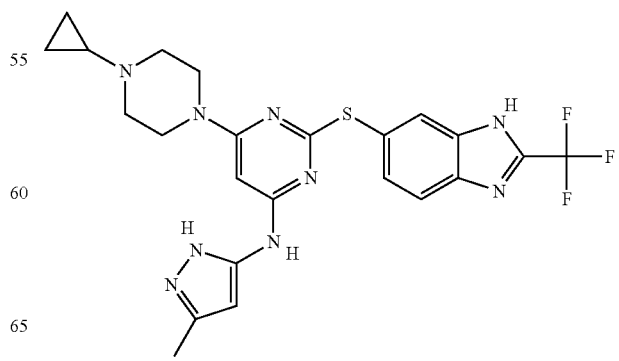

I-4

I-5
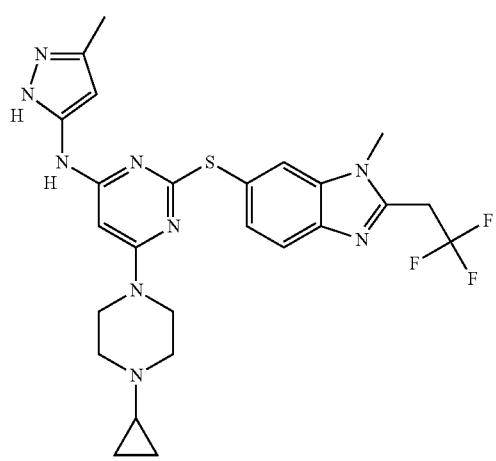
I-8
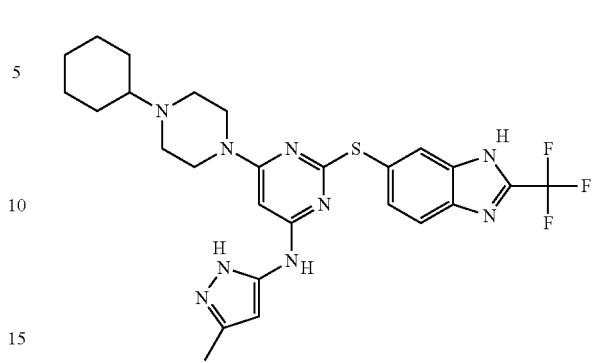
I-6
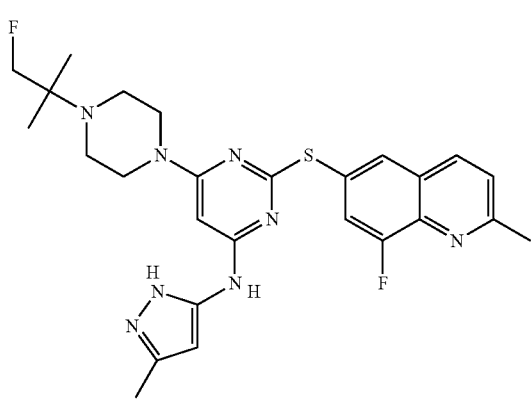
I-9
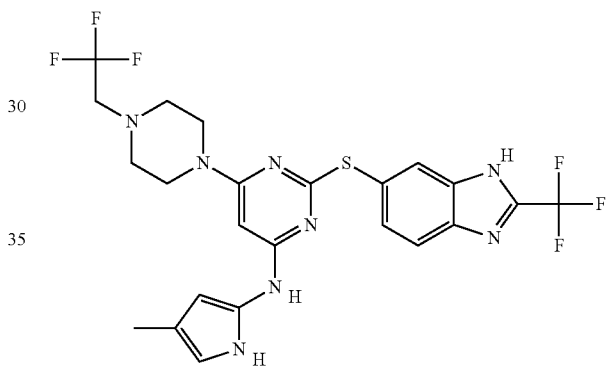
I-7
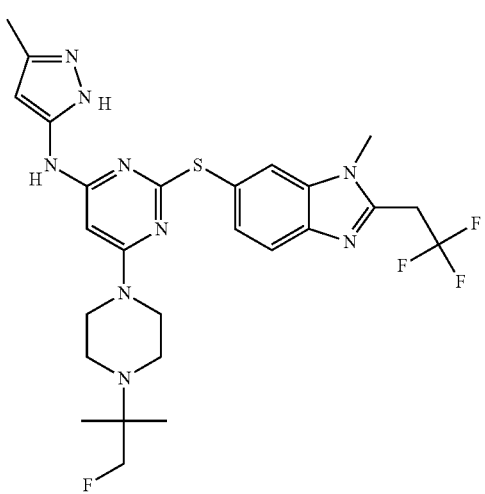
I-10
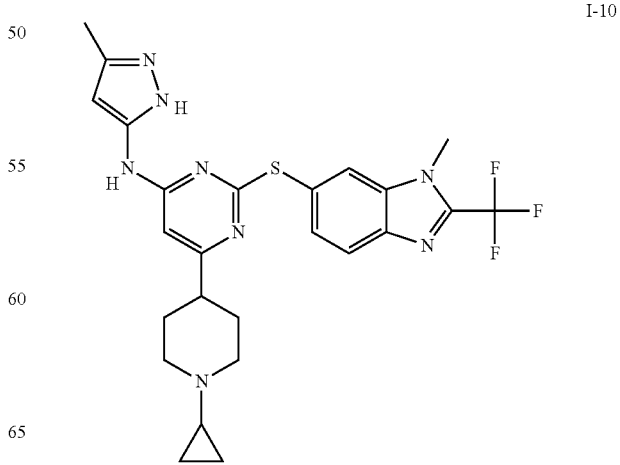

I-11
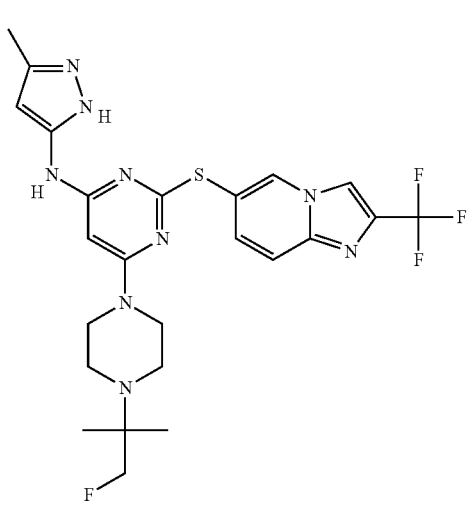
I-14
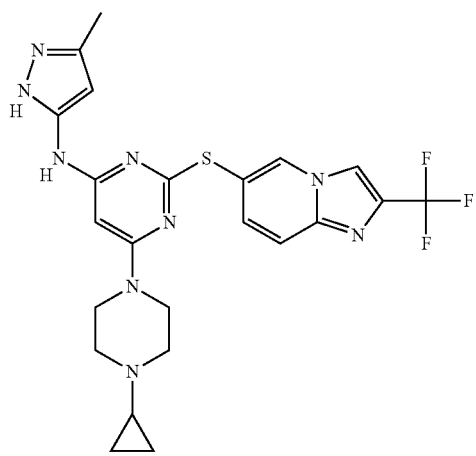
I-12
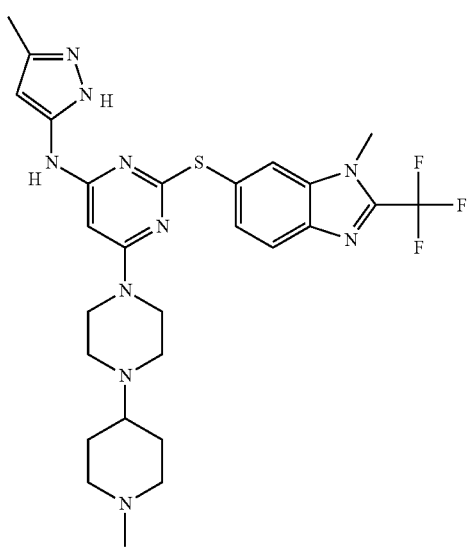
I-15
I-13
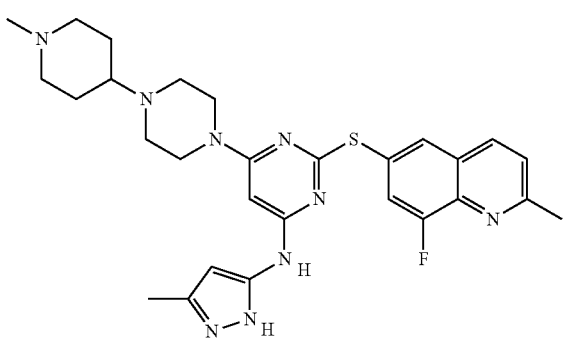
I-16
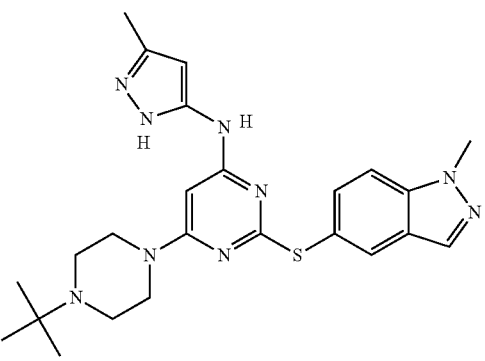

-continued
I-17
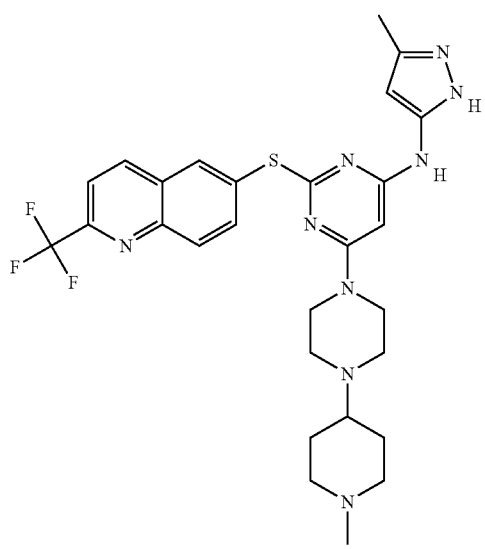
I-18
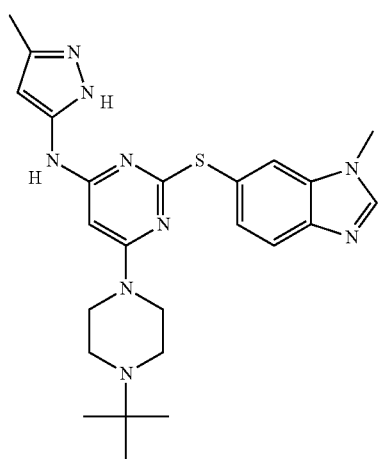
I-19
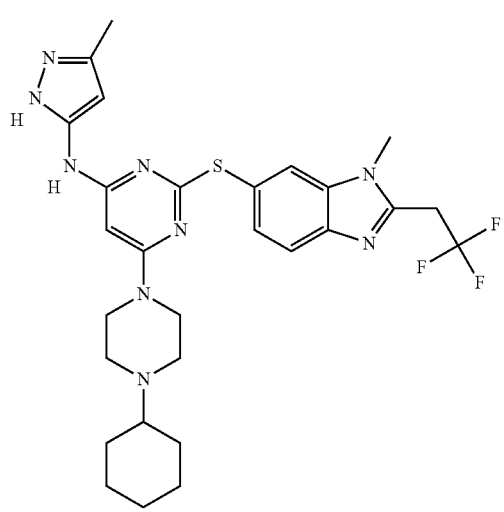
-continued
I-20
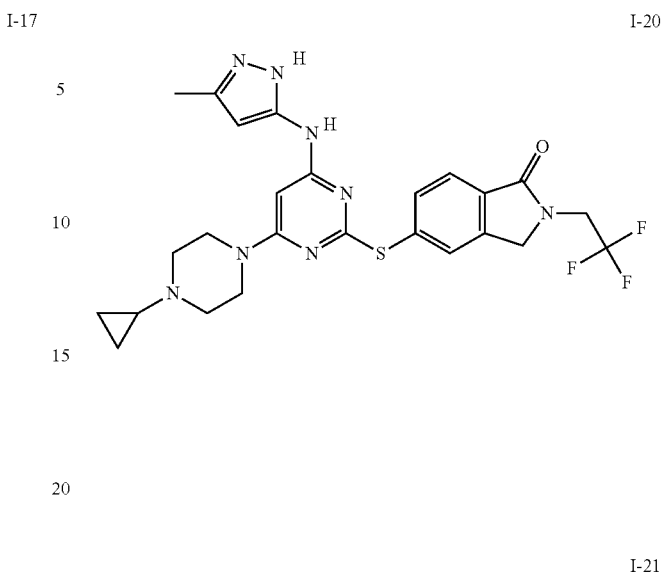
I-21
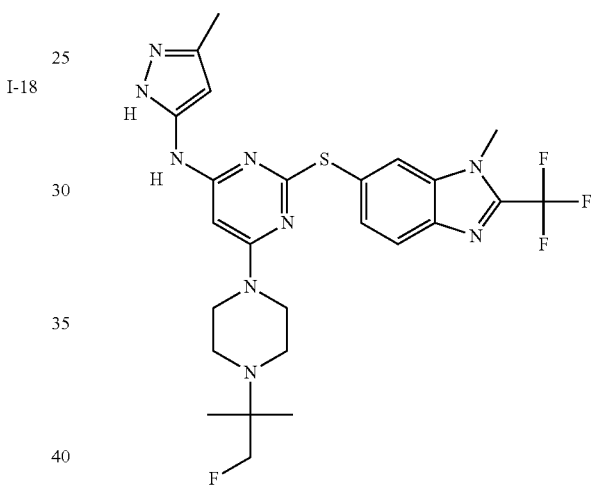
I-22
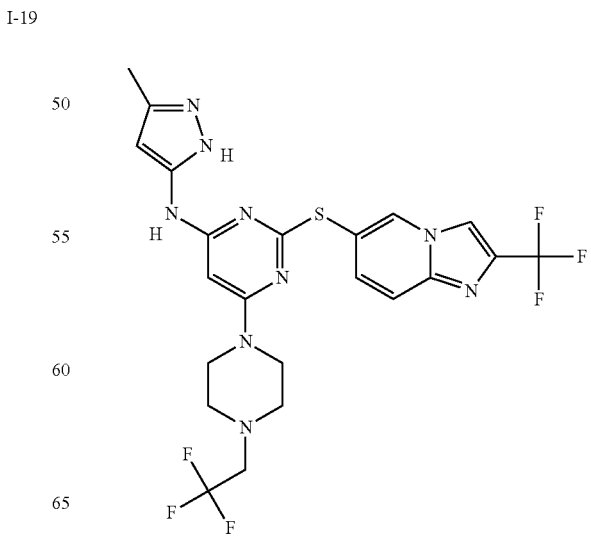

-continued

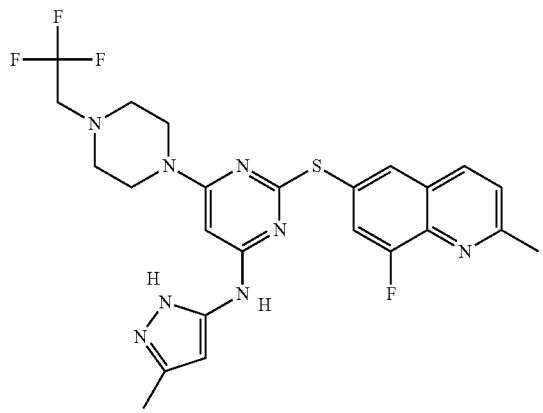

I-23

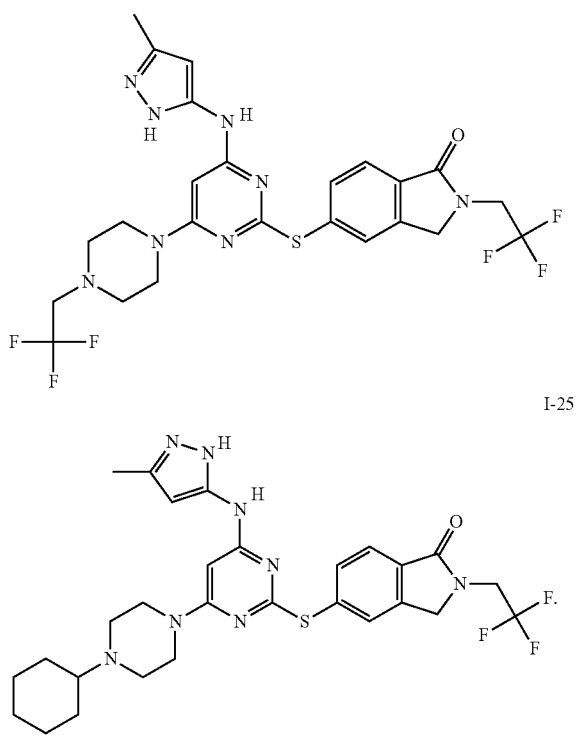

I-24

I-25

For purposes of this invention, the chemical elements are identified in accordance with the Periodic Table of the Elements, CAS version, Handbook of Chemistry and Physics, 75th Ed. Additionally, general principles of organic chemistry are described in texts known to those of ordinary skill in the art, including, for example, "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", and the like, as used herein, means an unbranched or branched, straight-chain or cyclic, substituted or unsubstituted hydrocarbon that is completely saturated or that contains one or more units of unsaturation that has a single point of attachment to the rest of the molecule. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl" and the like) refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "alkyl" as used herein, means an unbranched or branched, straight-chain or cyclic hydrocarbon that is completely saturated and has a single point of attachment to the rest of the molecule. Unless otherwise indicated, alkyl groups contain 1-12 carbon atoms. Specific examples of alkyl groups include, but are not limited to, methyl, ethyl, isopropyl, n-propyl, and sec-butyl.

In the compounds of this invention, rings include linearly-fused, bridged, or spirocyclic rings. Examples of bridged cycloaliphatic groups include, but are not limited to, bicyclo[3.3.2]decane, bicyclo[3.1.1]heptane, and bicyclo[3.2.2]nonane.

The term "heterocycle", "heterocyclyl", or "heterocyclic", and the like, as used herein means non-aromatic, monocyclic or bicyclic ring in which one or more ring members are an independently selected heteroatom. In some embodiments, the "heterocycle", "heterocyclyl", or "heterocyclic" group has three to ten ring members in which one or more ring members is a heteroatom independently selected from oxygen, sulfur, nitrogen, or phosphorus, and each ring in the system contains 3 to 7 ring members. Examples of bridged heterocycles include, but are not limited to, 7-aza-bicyclo[2.2.1]heptane and 3-aza-bicyclo[3.2.2]nonane.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

As used herein, the term "Ht" is interchangeable with "Het" and

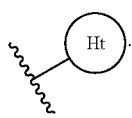

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "aryl" refers to monocyclic, or bicyclic ring having a total of five to twelve ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", refers to monocyclic or bicyclic ring having a total of five to twelve ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "unsaturated", as used herein, means that a moiety has one or more units of unsaturation.

The term "halogen" means F, Cl, Br, or I.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, and other editions of this book, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention. As would be understood by a skilled practitioner, a pyrazole group can be represented in a variety of ways. For example, a structure drawn as

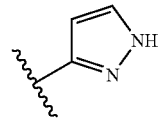 [SMILES: *c1cc[nH]n1]

also represents other possible tautomers, such as

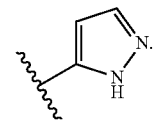 [SMILES: *c1ccn[nH]1]

Likewise, a structure drawn as

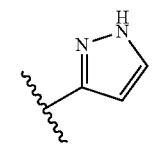

also represents other possible tautomers, such as

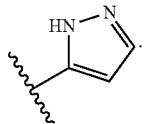

Unless otherwise indicated, a substituent can freely rotate around any rotatable bonds. For example, a substituent drawn as

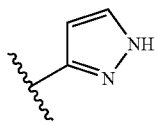 [SMILES: *c1cc[nH]n1]

also represents

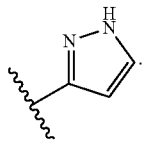

Likewise, a substituent drawn as

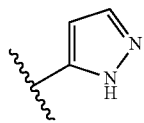 [SMILES: *c1ccn[nH]1]

also represents

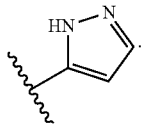 [SMILES: *c1ccn[nH]1]

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds of this invention may be prepared in light of the specification using steps generally known to those of ordinary skill in the art. Those compounds may be analyzed by known methods, including but not limited to LCMS (liquid chromatography mass spectrometry) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following scheme are as defined herein.

Scheme I

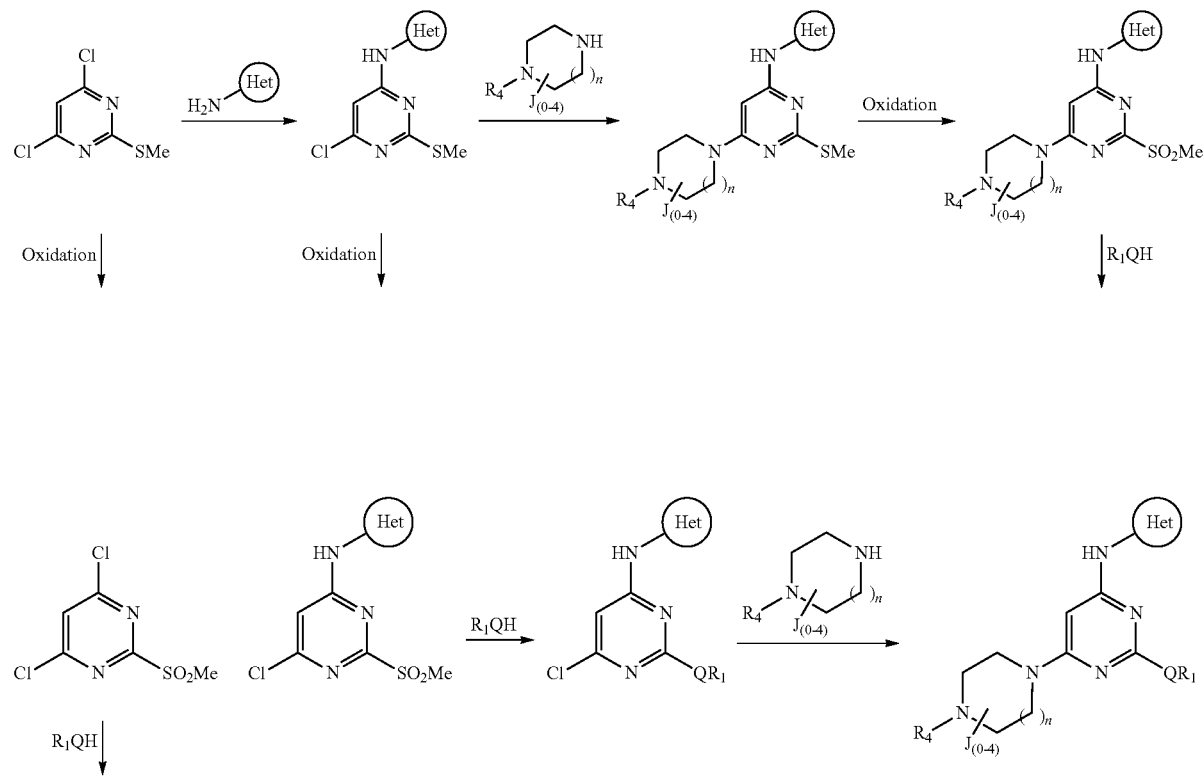

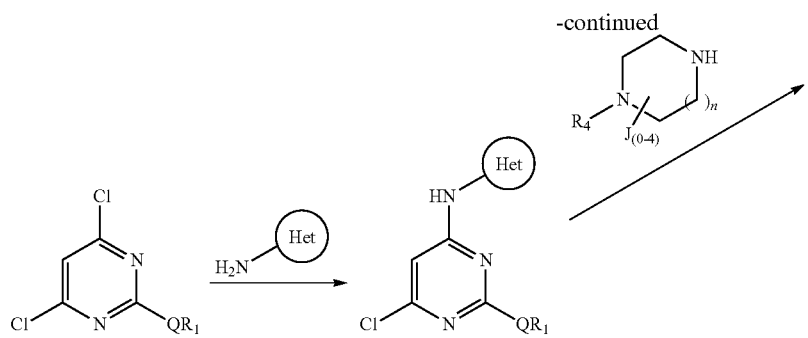

Scheme I above shows a generic method for making compounds of this invention. The compounds of this invention can be made in a variety of ways, as shown above. In essence, there are three main groups that are added to the dichloropyrimidine starting material. The order in which these groups are added can vary. The three main reactions involved are: addition of the piperazine or homopiperazine, addition of the amino-heteroaryl, and addition of -Q-$R^1$ (which includes the oxidation of —SMe into a suitable leaving group, e.g., $SO_2Me$). As shown above, the piperazine or homopiperazine, amino-heteroaryl, and -Q-$R^1$ can be added in various different orders. For instance, the amino-heteoaryl can be added first, followed by addition of the piperazine or homopiperazine, oxidation, and finally addition of -Q-$R^1$. Or instead, oxidation can occur first, followed by addition of -Q-$R^1$, addition of the amino-heteroaryl, and finally addition of the piperazine or homopiperazine. A skilled practitioner would understand the various reactions shown above.

Additionally, the compounds of this invention may be prepared according to the methods shown in WO 2004/000833.

Accordingly, this invention relates to processes for making the compounds of this invention.

Methods for evaluating the activity of the compounds of this invention (e.g., kinase assays) are known in the art and are also described in the examples set forth.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of the invention relates to inhibiting kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of kinase activity in a biological sample is useful for a variety of purposes that are known to one of skill in the art. Examples of such purposes include, but are not limited to, blood transfusion, organ-transplantation, biological specimen storage, and biological assays.

Inhibition of kinase activity in a biological sample is also useful for the study of kinases in biological and pathological phenomena; the study of intracellular signal transduction pathways mediated by such kinases; and the comparative evaluation of new kinase inhibitors.

The Aurora protein kinase inhibitors or pharmaceutical salts thereof may be formulated into pharmaceutical compositions for administration to animals or humans. These pharmaceutical compositions, which comprise an amount of the Aurora protein inhibitor effective to treat or prevent an Aurora-mediated condition and a pharmaceutically acceptable carrier, are another embodiment of the present invention.

The term "Aurora-mediated condition" or "Aurora-mediated disease" as used herein means any disease or other deleterious condition in which Aurora (Aurora A, Aurora B, and Aurora C) is known to play a role. Such conditions include, without limitation, cancer, proliferative disorders, and myeloproliferative disorders.

Examples of myeloproliferative disorders include, but are not limited, to, polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

The term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Such derivatives or prodrugs include those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Examples of pharmaceutically acceptable prodrugs of the compounds of this invention include, without limitation, esters, amino acid esters, phosphate esters, metal salts and sulfonate esters.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Base addition salts can be prepared by 1) reacting the purified compound in its acid form with a suitable organic or inorganic base and 2) isolating the salt thus formed.

Salts derived from appropriate bases include alkali metal (e.g., sodium and potassium), alkaline earth metal (e.g., magnesium), ammonium and N$^+$(C$_{1-4}$ alkyl)$_4$ salts. This invention also envisions the quaternization of any basic nitrogen-containing groups of the compounds disclosed herein. Water or oil-soluble or dispersible products may be obtained by such quaternization.

Base addition salts also include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraperitoneal, intrahepatic, intralesional and intracranial injection or infusion techniques.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, a bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used may include lactose and corn starch. Lubricating agents, such as magnesium stearate, may also be added. For oral administration in a capsule form, useful diluents may include lactose and dried cornstarch. When aqueous suspensions are required for oral use, the active ingredient may be combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials may include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations may be prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention may include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration, and the indication. In an embodiment, the compositions should be formulated so that a dosage of between 0.01-100 mg/kg body weight/day of the inhibitor can be administered to a patient receiving these compositions. In another embodiment, the compositions should be formulated so that a dosage of between 0.1-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing cancer, a proliferative disorder, or a myeloproliferative disorder comprising the step of administering to a patient one of the herein-described compounds or pharmaceutical compositions.

The term "patient", as used herein, means an animal, including a human.

In some embodiments, said method is used to treat or prevent a hematopoietic disorder, such as acute-myelogenous leukemia (AML), acute-promyelocytic leukemia (APL), chronic-myelogenous leukemia (CML), or acute lymphocytic leukemia (ALL).

In other embodiments, said method is used to treat or prevent myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

In yet other embodiments, said method is used to treat or prevent cancer, such as cancers of the breast, colon, prostate, skin, pancreas, brain, genitourinary tract, lymphatic system, stomach, larynx and lung, including lung adenocarcinoma, small cell lung cancer, and non-small cell lung cancer.

Another embodiment provides a method of treating or preventing cancer comprising the step of administering to a patient a compound of formula I or a composition comprising said compound.

Another aspect of the invention relates to inhibiting kinase activity in a patient, which method comprises administering to the patient a compound of formula I or a composition comprising said compound. In some embodiments, said kinase is an Aurora kinase (Aurora A, Aurora B, Aurora C), Abl, Arg, FGFR1, MELK, MLK1, MuSK, Ret, or TrkA.

Depending upon the particular conditions to be treated or prevented, additional drugs may be administered together with the compounds of this invention. In some cases, these additional drugs are normally administered to treat or prevent the same condition. For example, chemotherapeutic agents or other anti-proliferative agents may be combined with the compounds of this invention to treat proliferative diseases.

Another aspect of this invention is directed towards a method of treating cancer in a subject in need thereof, comprising the sequential or co-administration of a compound of this invention or a pharmaceutically acceptable salt thereof, and another therapeutic agent. In some embodiments, said additional therapeutic agent is selected from an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In yet other embodiments, said additional therapeutic agent is selected from camptothecin, doxorubicin, idarubicin, Cisplatin, taxol, taxotere, vincristine, tarceva, the MEK inhibitor, U0126, a KSP inhibitor, vorinostat, Gleevec, dasatinib, and nilotinib.

In another embodiment, said therapeutic agent is dasatinib.

In another embodiment, said therapeutic agent is nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxane®).

Other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, dexamethasone, and cyclophosphamide.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®) 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecare); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Another embodiment provides a simultaneous, separate or sequential use of a combined preparation.

Those additional agents may be administered separately, as part of a multiple dosage regimen, from the kinase inhibitor-containing compound or composition. Alternatively, those agents may be part of a single dosage form, mixed together with the kinase inhibitor in a single composition.

In order that this invention be more fully understood, the following examples are set forth. These examples are for the purpose of illustration only and are not to be construed as limiting the scope of the invention in any way. All documents cited herein are hereby incorporated by reference.

EXAMPLES

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm

Gradient: 0-100% acetonitrile+methanol 60:40 (20 mM Tris phosphate)

Flow rate: 1.5 mL/minute

Detection: 225 nm.

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions was 5%-100% acetonitrile-methanol over 3.5 mins gradient time and 5 mins run time on an ACE C8 3.0×75 mm column. Flow rate was 1.2 ml/min.

$^1$H-NMR spectra were recorded at 400 MHz using a Bruker DPX 400 instrument.

The following compounds of formula I were prepared according to the methods shown in the schemes and examples described herein. The compounds were also analyzed according to the methods described herein.

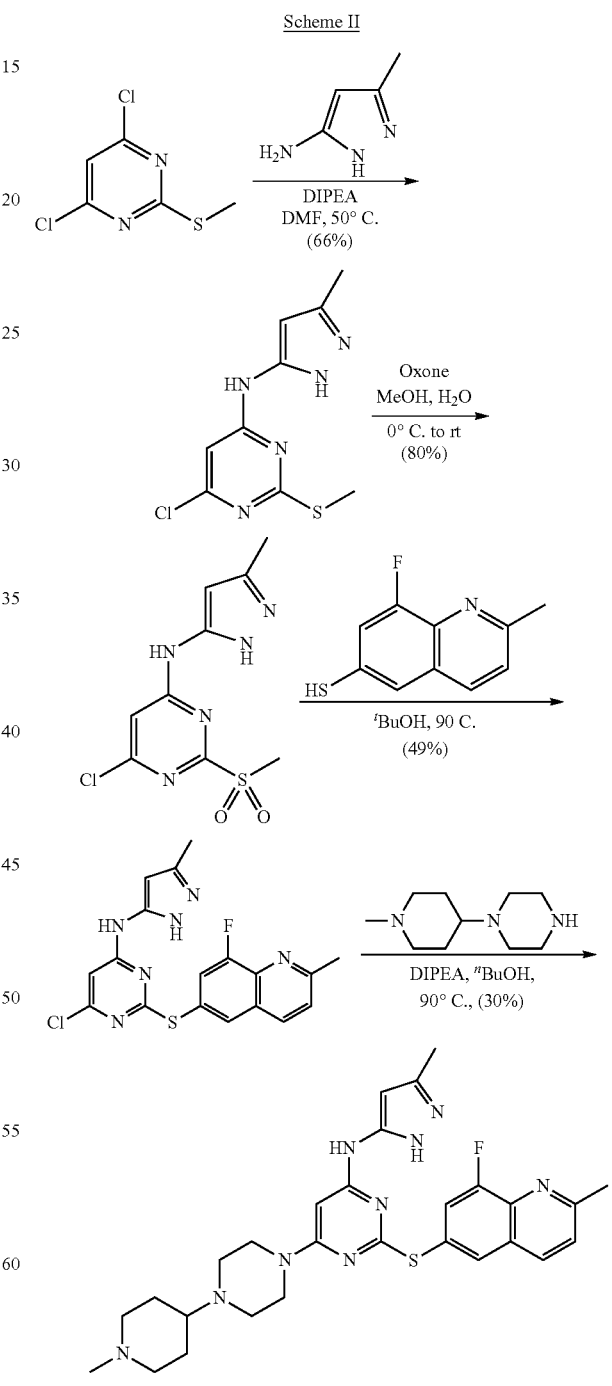

Scheme II

I-13

Example 1

2-(8-fluoro-2-methylquinolin-6-ylthio)-N-(3-methyl-1H-pyrazol-5-yl)-6-(4-(1-methylpiperidin-4-yl)piperazin-1-yl)pyrimidin-4-amine (I-13)

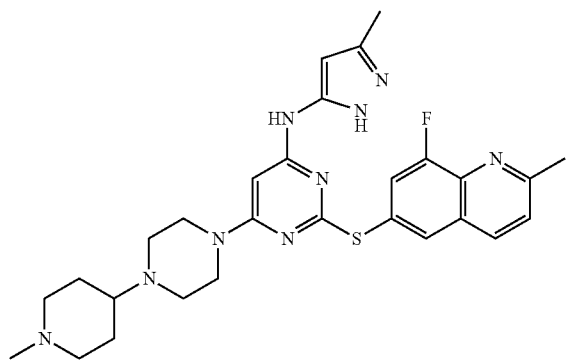

Method A: 6-chloro-N-(3-methyl-1H-pyrazol-5-yl)-2-(methylthio)pyrimidin-4-amine

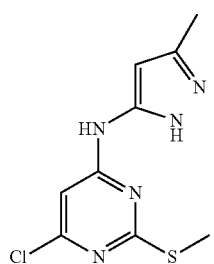 [SMILES: CSc1nc(Cl)cc(N/C(N)=C/C(C)=N)n1]

To a stirred solution of 4,6-dichloro-2-(methylthio)pyrimidine (25 g, 0.128 mol) in DMF (100 ml) was added diisopropylamine (19.8 g, 0.154 mol) followed by 3-amino-5-methylpyrazole (13.7 g, 0.154 mol) portionwise over 10 minutes. The solution was heated to 50° C. for 16 hours, after which time all of the starting material had reacted (by LC/MS analysis). The mixture was cooled to ambient and poured into water (250 ml). The precipitate was filtered and the wet solid slurried in diethyl ether (300 ml). The solid was again filtered and re-slurried in methanol (100 ml). The filtered product was air dried on the sinter, then further dried under vacuum to afford the title compound as an off-white solid (22.1 g, 66% yield). $^1$H NMR (DMSO D$^6$, 400 MHz) δ 2.22 (3H, s), 3.31 (3H, s), 6.00-7.50 (2H, br m), 10.17 (1H, s), 12.10 (1H, s); MS (ES$^+$) 256, (ES$^-$) 254.

Method B: 6-chloro-N-(3-methyl-1H-pyrazol-5-yl)-2-(methylsulfonyl)pyrimidin-4-amine

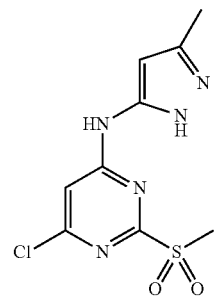 [SMILES: CC(=N)/C=C(\N)Nc1cc(Cl)nc(S(C)(=O)=O)n1]

To a stirred solution of 6-chloro-N-(3-methyl-1H-pyrazol-5-yl)-2-(methylthio)pyrimidin-4-amine (8 g, 31.19 mmol) in MeOH (200 ml) cooled in an ice bath was added portionwise a slurry of oxone (44 g, 71.73 mmol) in water (100 ml) over 10 minutes. The reaction mixture was stirred at this temperature for a further 30 minutes before being allowed to warm up to room temperature for 2 hours. The solid, isolated by filtration, was stirred vigorously in a 1:1 mixture of water and saturated bicarbonate solution. The solid was then filtered and dried in a pistol under vacuo to afford the title compound as a yellow solid (7.17 g, 80% yield). $^1$H NMR (DMSO D$^6$, 400 MHz) δ2.23 (3H, s), 3.32 (3H, s), 5.80-8.10 (2H, br m), 10.92 (1H, br s), 12.26 (1H, br s); MS (ES$^+$) 288, (ES$^-$) 286.

Method C: 6-chloro-2-(8-fluoro-2-methylquinolin-6-ylthio)-N-(3-methyl-1H-pyrazol-5-yl)pyrimidin-4-amine

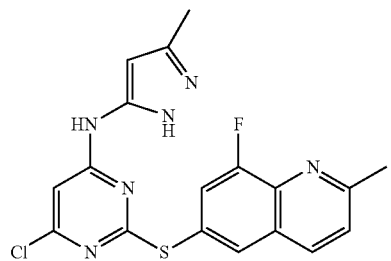 [SMILES: CC(=N)/C=C(\N)Nc1cc(Cl)nc(Sc2cc(F)c3nc(C)ccc3c2)n1]

To a stirred solution of 8-fluoro-2-methylquinoline-6-thiol (1.21 g, 6.27 mmol) in $^t$BuOH (25 ml) was added 6-chloro-N-(3-methyl-1H-pyrazol-5-yl)-2-(methylsulfonyl)pyrimidin-4-amine (1.5 g, 5.22 mmol). The reaction mixture was degassed three times (vacuum/N$_2$) before being heated to 90° C. for 18 hours. The crude mixture was partially concentrated in vacuo. The resulting solid was filtered and washed with ethyl acetate and an aqueous solution of K$_2$CO$_3$. The solid was dried in a pistol under vacuo to afford the title compound as an off-white solid (1.029 g, 49% yield). $^1$H NMR (DMSO D$^6$, 400 MHz) δ1.42 (3H, br s), 2.73 (3H, s), 4.95 (1H, br s), 6.47 (1H, br s), 7.61 (1H, d), 7.78 (1H, dd), 8.14 (1H, s), 8.39 (1H, d), 10.32 (1H, br s), 11.75 (1H, br s); MS (ES+) 401, (ES−) 399.

Method D: 2-(8-fluoro-2-methylquinolin-6-ylthio)-N-(3-methyl-1H-pyrazol-5-yl)-6-(4-(1-methylpiperidin-4-yl)piperazin-1-yl)pyrimidin-4-amine

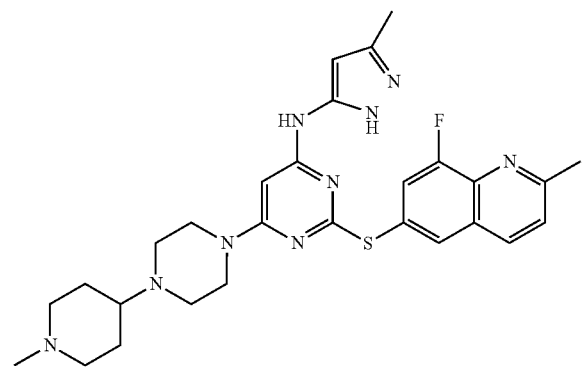

To a stirred mixture of 6-chloro-2-(8-fluoro-2-methylquinolin-6-ylthio)-N-(3-methyl-1H-pyrazol-5-yl)pyrimidin-4-amine (200 mg, 0.5 mmol), 1-(1-methylpiperidin-4-yl)piperazine (367 mg, 2 mmol) and diisopropylethylamine (194 mg, 1.5 mmol) in ⁿBuOH (5 ml) was heated to 90° C. for 18 hours. The crude mixture was concentrated in vacuo and the residue was partitioned between ethyl acetate and water. The organic layer was further extracted with water. The combined organic layers were washed with brine, dried over MgSO$_4$ and concentrated in vacuo. The resulting residue was triturated with cold acetonitrile, filtered and dried to afford the title compound as an off-white solid (83 mg, 30% yield).

$^1$H NMR (DMSO D$^6$, 400 MHz) δ 1.35-1.50 (2H, m), 1.64-1.90 (6H, m), 2.10-2.18 (4H, m), 2.45-2.54 (6H, m), 2.70-2.84 (5H, m), 3.35 (3H, m), 5.33 (1H, br s), 6.12 (1H, br s), 7.57 (1H, d), 7.71 (1H, d), 8.05 (1H, s), 8.38 (1H, d), 9.25 (1H, s), 11.67 (1H, s); MS (ES+) 548, (ES−) 546.

The various R$^y$H moieties used in the preparation of compounds of formula I are described in the literature (see, for example, Poindexter, G. S.; Bruce, M. A.; LeBoulluec, K. L.; Monkovic, I. *Tetrahedron Lett.*, 1994, 35, 7331 for the synthesis of 1-cyclohexylpiperazine and 1-tert-butylpiperazine; Zaragoza, F.; Stephensen, H.; Knudsen, S. M.; Pridal, L.; Wulff, B. S.; Rimvall, K. *J. Med. Chem.*, 2004, 47, 2833 for the synthesis of 1-cyclopropylpiperazine) or can be prepared following procedures similar to the ones described below for the synthesis of 1-(2,2,2-trifluoroethyl)piperazine dihydrobromide salt.

Scheme III

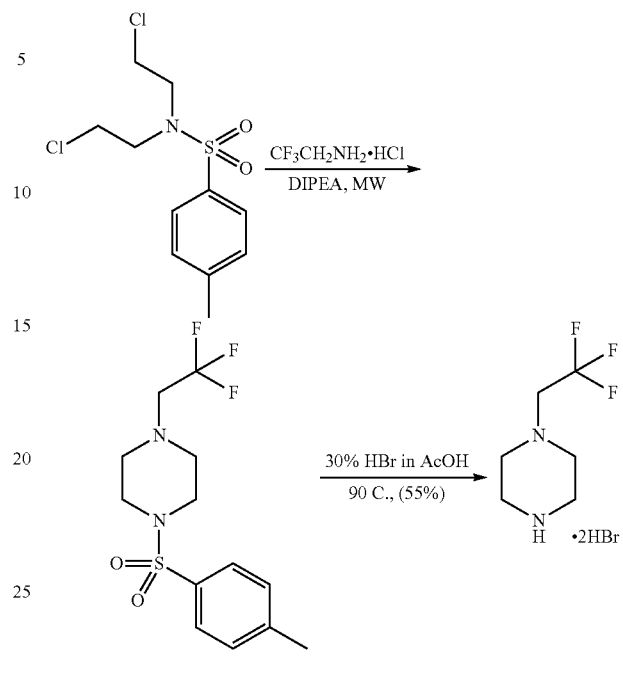

Example 2

1-(2,2,2-trifluoroethyl)piperazine dihydrobromide salt

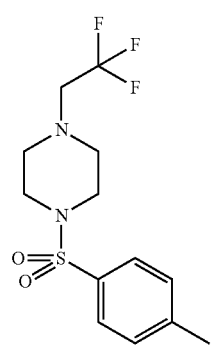 [SMILES: Cc1ccc(S(=O)(=O)N2CCN(CC(F)(F)F)CC2)cc1]

Method E: 1-tosyl-4-(2,2,2-trifluoroethyl)piperazine

A mixture of 1-(1,5-dichloropentan-3-ylsulfonyl)-4)methylbenzene (1.5 g, 5 mmol), trifluoromethylmethylamine HCl salt (1.35 g, 10 mmol) in diisopropylethylamine (15 ml) was stirred at 160° C. in a CEM microwave for 50 minutes. The residue was diluted with ethyl acetate. The organic layer was washed with water and brine, dried over magnesium sulfate and concentrated under reduced pressure. The residue was triturated in diethyl ether. A white solid was collected by filtration (730 mg, 45% yield). $^1$H NMR (CDCl$_3$, 400 MHz) 2.45 (3H, s), 2.82-2.86 (4H, m), 2.90-3.00 (2H, qd), 3.01-3.05 (4H, m), 7.30-7.35 (2H, d), 7.60-7.65 (2H, d); MS (ES$^+$) 323.

Method F: 1-(2,2,2-trifluoroethyl)piperazine dihydrobromide salt

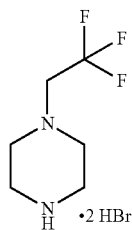 [SMILES: FC(F)(F)CN1CCNCC1]

A suspension of 1-tosyl-4-(2,2,2-trifluoroethyl)piperazine (700 mg, 2.2 mmol) in a 30% HBr/acetic acid solution was stirred at 90° C. for 90 minutes. Toluene was added to the suspension. An orange solid was filtered off and washed with diethyl ether to afford the desired compound (400 mg, 55% yield) as a bis HBr salt.

The various HQ-R$^1$ moieties used in the preparation of compounds of formula I wherein Q is a sulfur atom can be prepared from their respective bromo- or iodo-derivatives. These halo intermediates are either described in the literature (See for example WO2005/111047 for the synthesis of 6-bromo-2-trifluoromethyl-imidazo[1,2-a]pyridine; Keller, H.; Schlosser, M. *Tetrahedron*, 1996, 52, 4637 for the synthesis of 6-bromo-2-(trifluoromethyl)quinoline) or prepared following procedures similar to the ones described below.

Example 3

1-methyl-2-(trifluoromethyl)-1H-benzo[d]imidazole-6-thiol

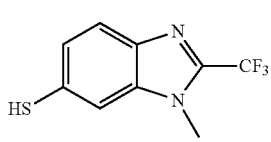

Method G: N$^1$-methyl-5-nitrobenzene-1,2-diamine

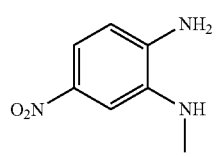

A 1 L round bottom flask was charged with 4-nitrobenzene-1,2-diamine (40 g, 0.26 mol), methyl iodide (13 ml, 0.21 mol) and DMF (300 ml), followed by the addition of saturated sodium carbonate (60 ml) over 2-3 minutes under rapid stirring. After stirring overnight at room temperature the reaction mixture was filtered and then concentrated in vacuo to a dark red oil. The residue was purified by flash column chromatography (15 to 30% ethyl acetate/petrol) to afford the title compound (27 g, 61% yield).

$^1$H NMR (DMSO D$^6$, 400 MHz) 1.8 (1H, br s), 2.90 (3H, d), 3.90 (2H, br s), 6.65 (1H, d), 7.50 (1H, s), 7.68 (1H, d); MS (ES$^+$) 168.

Method H: 1-methyl-6-nitro-2-(trifluoromethyl)-1H-benzo[d]imidazole

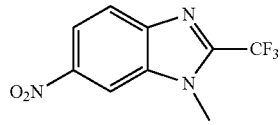

A 250 ml round bottomed flask was charged with N$^1$-methyl-5-nitrobenzene-1,2-diamine (29 g, 0.16 mol), trifluoroacetic acid (22 ml, 0.24 mol) and a few drops of concentrated HCl. A minimum amount of DCM (~20 ml) was added so that the solid mixture was stirring. The reaction mixture was heated to 70° C. for 12 hours forming a dark brown liquid. The reaction mixture was allowed to cool to room temperature, basified by the slow addition of saturated bicarbonate solution, and extracted into ethyl acetate. The aqueous layer was further extracted twice with ethyl acetate. The organic layers were combined, dried over magnesium sulfate, filtered and concentrated in vacuo. The compound was purified by flash column chromatography (10 to 20% ethyl acetate/petrol) to afford the title compound (8 g, 20% yield). $^1$H NMR (DMSO D$^6$, 400 MHz) 4.2 (3H, s), 8.05 (1H, d), 8.35 (1H, d), 8.55 (1H, s); MS (ES$^+$) 246.

Method I: 1-methyl-2-(trifluoromethyl)-1H-benzo[d]imidazol-6-amine

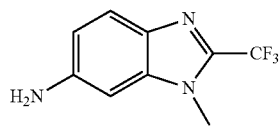 [SMILES: Cn1c(C(F)(F)F)nc2ccc([N+](=O)[O-])cc21]

A 250 ml round bottomed flask was charged with 1-methyl-6-nitro-2-(trifluoromethyl)-1H-benzo[d]imidazole (6 g, 24 mmol) and concentrated HCl (40 ml). Once the solution has become clear, water (~15 ml) was added until the solution just started to become cloudy. SnCl$_4$ (27 g, 120 mmol) was added in portions over 5 minutes (caution exotherm!). Initial exotherm caused the temperature to rise to 60° C. The reaction mixture was stirred and allowed to cool down to room temperature. After 1 hour, the reaction mixture was diluted with water (100 ml), basified with 1M NaOH and extracted twice with ethyl acetate. The organic layers were combined, washed with brine, dried over magnesium sulfate and concentrated in vacuo to afford the title compound as a dark coloured solid. (5 g, 100% yield). $^1$H NMR (DMSO D$^6$, 400 MHz) 3.75 (3H, s), 4.6 (2H, br s), 6.65 (1H, s), 6.7 (1H, d), 7.75 (1H, d); MS (ES$^+$) 215.

Method J: 6-iodo-1-methyl-2-(trifluoromethyl)-1H-benzo[d]imidazole

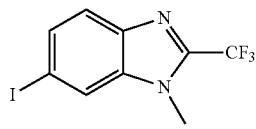

A 250 ml round bottomed flask was charged with 1-methyl-2-(trifluoromethyl)-1H-benzo[d]imidazol-6-amine (800 mg, 3.7 mmol), and water (10 ml) and cooled in an ice bath. Concentrated sulfuric acid (1.5 ml) was added dropwise followed by the slow addition of sodium nitrite (270 mg, 3.9 mmol) as an aqueous solution (3 ml). The reaction was stirred at 0° C. for another 5 minutes and then transferred to a dropping funnel. This reaction mixture was then added dropwise over 10 minutes to a cooled solution of KI in water (10 ml). After addition was complete the reaction was allowed to warm up to room temperature. The reaction mixture was diluted with water (10 ml), basified with bicarbonate solution and extracted twice with ethyl acetate. The organic layers were combined, washed with brine, dried over magnesium sulfate and concentrated in vacuo. The residue was purified by flash column chromatography (10 to 20% ethyl acetate/petrol) to afford the title compound (600 mg, 48% yield). $^1$H NMR (DMSO D$^6$, 400 MHz) 3.8 (3H, s), 4.6 (2H, br s), 7.55 (1H, s), 7.6 (1H, d), 7.75 (1H, d); MS (ES$^+$) 326.

Method K: 1,2-bis(1-methyl-2-(trifluoromethyl)-1H-benzo[d]imidazol-6-yl)disulfane

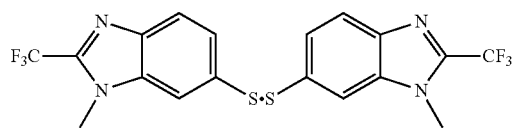

A 250 ml round bottomed flask was charged with 6-iodo-1-methyl-2-(trifluoromethyl)-1H-benzo[d]imidazole (2 g, 6.1 mmol), thiourea (1.35 g, 18 mmol), nickel on silica (400 mg) and NMP (20 ml). The mixture was heated overnight at 140° C. The reaction mixture was then allowed to cool down, filtered through celite, diluted with ethyl acetate and washed twice with water and brine. The organic layer was dried over magnesium sulfate, filtered and concentrated in vacuo. The residue was purified by flash column chromatography (10% ethyl acetate/petrol) to afford the desired product (1.1 g, 38% yield). $^1$H NMR (DMSO D$^6$, 400 MHz) 3.9 (3H, s), 7.45 (0.5H, d), 7.5 (0.5H, d), 7.62 (1H, d), 7.83 (0.5H, s), 7.85 (1H, s); MS (ES$^+$) 462.

Method L: 1-methyl-2-(trifluoromethyl)-1H-benzo[d]imidazole-6-thiol

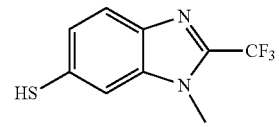

Tris-(2-carboxyethyl)phosphine hydrochloride (TCEP.HCl, 650 mg, 2.2 mmol) was added to a solution of 1,2-bis(1-methyl-2-(trifluoromethyl)-1H-benzo[d]imidazol-6-yl)disulfane (1 g, 2.2 mmol) and disopropylethylamine (0.4 ml, 2.1 mmol) in a mixture of water and dimethylformamide (2 ml/10 ml). The reaction mixture was stirred at room temperature for 120 minutes. The reaction mixture was diluted with ethyl acetate, and then washed with brine. The organic layer was dried over magnesium sulfate and concentrated in vacuo to afford the compound as a white solid. MS (ES$^+$) 233.

Example 4

8-fluoro-2-methylquinoline-6-thiol

Method M: 6-bromo-8-fluoro-2-methylquinoline

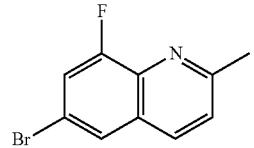

2-Fluoro-4-bromoaniline (10 g, 0.053 mol) was slurried in 6M HCl (100 ml). The mixture was heated to reflux and crotonaldehyde (14.9 g, 0.212 mol) was added dropwise over 1 hour. The resulting mixture was heated for an additional 90 minutes, then cooled down to room temperature and neutralized by careful addition of concentrated ammonia solution. The mixture was extracted with ethyl acetate and the organic layer was washed with water and brine, dried over magnesium sulfate, filtered and concentrated in vacuo. The residue was purified by flash column chromatography, eluting with 15-10% ethyl acetate/petrol. The product containing fractions were combined and concentrated to ca 60 ml. The product was then isolated by filtration. The filter cake was washed with petrol and air dried to afford the title compound as a solid (5.96 g, 47% yield). $^1$H NMR (CDCl$_3$, 400 MHz) 2.80 (3H, s), 7.38 (1H, d), 7.53 (1H, d), 7.76 (1H, s), 8.00 (1H, d); MS (ES$^+$) 240/242.

Method N: 8-fluoro-2-methylquinoline-6-thiol

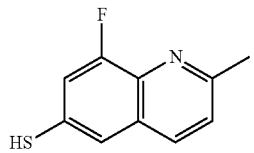

Triisopropylsilane thiol (3.4 g, 0.018 mol) was dissolved in anhydrous THF (30 ml). The mixture was cooled in an ice bath and sodium hydride (60% suspension, 752 mg, 0.0188 mol) was added portionwise. The mixture was stirred for 30 minutes. Dry toluene (30 ml) was then added followed by 6-bromo-8-fluoro-2-methylquinoline (4.3 g, 0.0179 mol) and tetrakispalladium triphenylphosphine (2.07 g). The reaction mixture was heated to 90° C. for 90 minutes then cooled to room temperature and diluted with ethyl acetate/water. The organic phase was removed and washed with water and brine, dried over magnesium sulfate, filtered and concentrated in vacuo. The residue was purified by flash column chromatography, eluting with 30-40% ethyl acetate/petrol. This gave initially the silyl protected thiol (2.82 g). Further elution afforded the required thiol (1.22 g, 35% yield). $^1$H NMR (CDCl$_3$, 400 MHz) 2.78 (3H, s), 3.69 (1H, s), 7.28-7.35 (2H, m), 7.47 (1H, s), 7.93 (1H, d); MS (ES$^+$) 194, (ES$^-$) 192.

Example 5

5-mercapto-2-(2,2,2-trifluoroethyl)isoindolin-1-one

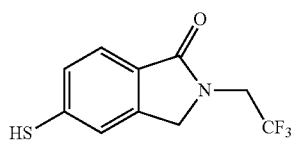

Method O: 4-bromo-2-(hydroxymethyl)-N-(2,2,2-trifluoroethyl)benzamide

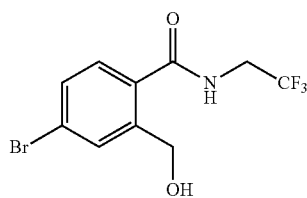 [SMILES: O=C(NCC(F)(F)F)c1ccc(Br)cc1CO]

To a stirred suspension of aluminium trichloride (4.07 g, 30.5 mmol) in dichloroethane (60 ml) cooled to 5° C. under a nitrogen atmosphere was added the solution of trifluoroethylamine (5.84 g, 38.7 mmol) at such a rate to keep the temperature of the reaction mixture below 10° C. After complete addition the reaction mixture was allowed to warm up to room temperature and stirred at this temperature for 4 hours. After this time bromophthalide powder (5 g, 23.5 mmol) was added in one portion and the reaction mixture was then heated to 80° C. for 18 hours. TLC showed complete conversion from starting material to product and the reaction was carefully quenched with iced water (100 ml) and stirred for 30 minutes until all the ice melted. Dichloromethane was added and the mixture was filtered through a pad of silica and washed with copious amounts of DCM to remove the aluminium residues. The filtrate was separated and the aqueous layer was further extracted with DCM (2×100 ml). The organic layers were combined and dried over magnesium sulfate, filtered and concentrated under reduced pressure to afford the title compound as an off-white powder (3.37 g, 46% yield). $^1$H NMR (DMSO D$^6$, 400 MHz) 4.02-4.11 (2H, m), 4.60-4.61 (2H, m), 5.43-5.46 (H, m), 7.36-7.39 (H, d), 7.55-7.57 (H, m), 7.76 (H, s) and 9.09-9.12 (H, m); MS (ES$^+$) 312, (ES$^-$) 310.

Method P:
5-bromo-2-(2,2,2-trifluoroethyl)isoindolin-1-one

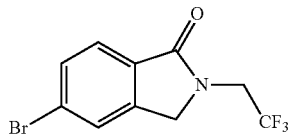 [SMILES: O=C1c2ccc(Br)cc2CN1CC(F)(F)F]

To a stirred solution of 4-bromo-2-(hydroxymethyl)-N-(2,2,2-trifluoroethyl)benzamide (3.37 g, 10.8 mmol) in anhydrous tetrahydrofuran (50 ml), N-methyl-2-pyrrolinone (20 mL), cooled to 5° C. under a nitrogen atmosphere was added a solution of 2M isopropyl magnesium chloride in anhydrous THF (25 ml) at such a rate to keep the temperature of the reaction mixture under 10° C. After complete addition, approximately 45 minutes, the reaction mixture was stirred at this temperature for an additional 60 minutes, and then at room temperature for 60 minutes. After that time, the reaction mixture was cooled down to 5° C. and a solution of bis (dimethylamino)phosphoryl chloride (1.85 g, 14.1 mmol) was added dropwise. No exotherm was observed and the reaction was heated at reflux for 72 hours once the addition was complete. After this time no starting material was observed by both TLC and LCMS and the reaction mixture was carefully quenched with water, and acidified with 1M aqueous hydrochloric acid. The aqueous was extracted with ethyl acetate (3×100 ml) and the organic layers were combined and dried over magnesium sulfate, filtered and concentrated under reduced pressure to leave a mobile oil which was purified by column chromatography eluting with 20% ethyl acetate/petroleum ether to afford the title compound as a white solid (2.81 g, 88% yield). $^1$H NMR (DMSO D$^6$, 400 MHz) 4.36-4.43 (2H, m), 4.62 (2H, s), 7.68-7.74 (2H, m) and 7.93 (1H, s); MS (ES$^+$) 296, (ES$^-$) 292.

Method Q: 2-(2,2,2-trifluoroethyl)-5-(triisopropylsilylthio)-isoindolin-1-one

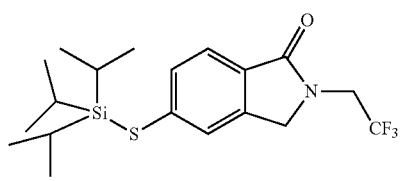 [SMILES: CC(C)[Si](Sc1ccc2c(c1)CN(CC(F)(F)F)C2=O)(C(C)C)C(C)C]

To a stirred solution of triisopropylsilane thiol (648 mg, 3.4 mmol) in anhydrous THF (10 ml), cooled to 5° C. under a nitrogen atmosphere was added 60% sodium hydride powder (143 mg, 3.57 mmol) portionwise over 10 minutes. The resulting yellow solution was stirred for 20 minutes and then a solution of 5-bromo-2-(2,2,2-trifluoro-ethyl)-2,3-dihydro-isoindol-1-one (1 g, 3.4 mmol) in anhydrous THF (10 ml) and Tetrakis(triphenylphosphine)palladium(0) (393 mg 0.34 mmol) was added. The reaction mixture was degassed with nitrogen and heated at 90° C. for 2 hours. After this time, tlc showed a mixture of starting material, product, and unprotected thiol. The mixture was concentrated in vacuo and the residue was purified on silica by flash column chromatography eluting with 30% ethyl acetate in petroleum ether to isolate both the protected (406 mg, 30% yield) and the non-protected thiol (171 mg, 20% yield). MS (ES$^+$) 248, (ES$^-$) 246 in both cases.

Method R: 5-mercapto-2-(2,2,2-trifluoroethyl)isoindolin-1-one

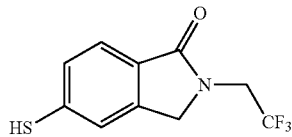

2-(2,2,2-trifluoroethyl)-5-(triisopropylsilylthio)-isoindolin-1-one (1.39 g, 3.45 mmol) was dissolved in a solution of hydrochloric acid (6.7 ml, 1.25 M, 8.62 mmol) in methanol (10 ml) and tetrahydrofuran (10 ml) and stirred at room temperature for 2 hours. The reaction mixture was concentrated in vacuo to afford the desired compound as an off-white solid (0.783 g, 92% yield). $^1$H NMR (CDCl$_3$, 400 MHz) 3.70 (1H, s), 4.22 (2H, q), 4.53 (2H, s), 7.35-7.39 (2H, m) and 7.76 (1H, d); MS (ES$^+$) 248, (ES$^-$) 246.

Example 6

1-methyl-1H-indazole-5-thiol

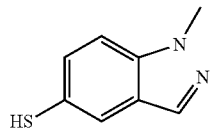

Method s: 5-iodo-1-methyl-1H-indazole

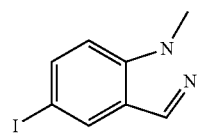

To 1-Methyl-1H-indazol-5-amine (500 mg, 3.40 mmol) in a mixture of concentrated sulfuric acid (1.3 ml) and water (5.5 ml) cooled down to 0° C., was added dropwise a solution of sodium nitrite (258 mg, 3.74 mmol) in water (0.5 ml). The reaction mixture was stirred at 0° C. for 10 minutes then added dropwise to a solution of sodium iodide (1.5 g) in water (4.5 ml) cooled to 0° C. After complete addition, the reaction mixture was heated to 90° C. for an additional 20 minutes. The resultant mixture was basified with a diluted solution of sodium hydroxide and extracted with ethylacetate. The organic phase was washed further with brine, dried over magnesium sulfate and concentrated in vacuo. The residue was purified on silica gel by flash column chromatography eluting with 20% EtOAc in petroleum ether to afford the title compound (475 mg, 54% yield). $^1$H NMR (DMSO D$^6$, 400 MHz) 4.03 (3H, s), 7.52 (1H, d), 7.63 (1H, dd), 7.99 (1H, s), 8.17 (1H, s).

Method t: 1-methyl-1H-indazole-5-thiol

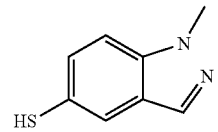

A mixture of 5-iodo-1-methyl-1H-indazole (190 mg, 0.70 mmol) and thiourea (112 mg, 1.50 mmol) was dissolved in NMP (1 ml) and heated to 50° C. The reaction mixture was degassed and nickel on silica (20 mg) was added. The reaction mixture was degassed again, then, warmed up to 150° C. for 4 hours. The reaction mixture was allowed to cool down, diluted with methanol and 4 ml of NMP. The resultant suspension was filtered through glass paper. The filtrate was concentrated in vacuo.

To the crude disulfide and disopropylethylamine (67 µl, 0.39 mmol) in a mixture of water and dimethylformamide (1 ml/5 ml) was added tris-(2-carboxyethyl)phosphine hydrochloride (TCEP.HCl, 222 mg, 0.78 mmol). The reaction mixture was stirred at room temperature for 120 minutes. The reaction mixture was diluted with ethyl acetate, then washed with brine. The organic layer was dried over magnesium sulfate and concentrated in vacuo to afford the compound as a white solid. $^1$H NMR (DMSO D$^6$, 400 MHz) 4.01 (3H, s), 5.34 (1H, s), 7.32 (1H, dd), 7.57 (1H, d), 7.69 (1H, s), 7.94 (1H, s); MS (ES$^+$) 165.

Example 7

Method U:
2-(trifluoromethyl)imidazo[1,2-a]pyridine-6-thiol

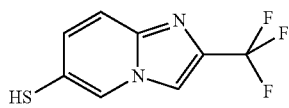 [SMILES: FC(F)(F)c1cn2cc(S)ccc2n1]

A mixture of 6-bromo-2-(trifluoromethyl)imidazo[1,2-a]pyridine (500 mg, 1.89 mmol) (for the synthesis, see WO2005111047) and sodium thiomethoxide (400 mg, 5.67 mmol) in dimethylacetamide (5 ml) was heated to 150° C. for 90 minutes under a nitrogen atmosphere. The resultant mixture was cooled down to room temperature and partitioned between ethyl acetate and an aqueous solution of ammonium chloride. The aqueous phase was extracted with more ethyl acetate and the combined organic layers were washed with water and brine, dried over magnesium sulfate and concentrated in vacuo to afford the title compound as a red oil (251 mg, 61% yield). MS (ES$^+$) 219, (ES$^+$) 217.

Table 2 below depicts data for compounds of Table 1. Compound numbers correspond to those compounds depicted in Table 1.

TABLE 2

| Compound No | M + 1 (obs) | 1H NMR | Rt (mins) |
|---|---|---|---|
| I-1 | 533 | (d6-DMSO, 400 MHz) 1.00-1.15 (2H, m), 1.18-1.45 (4H, m), 1.50-1.60 (2H, m), 1.75-1.80 (2H, m), 2.00-2.10 (5H, m), 2.65-2.70 (3H, m), 3.05-3.25 (5H, m), 3.40-3.50 (2H, m), 4.10-4.20 (2H, m), 5.20-5.30 (1H, s), 6.05-6.25 (1H, br s), 7.55-7.60 (1H, d), 7.70-7.75 (1H, d), 8.07 (1H, s), 8.37-3.90 (1H, d), 9.40-9.50 (2H, m) | 3.84 |
| I-2 | 579 | (d6-DMSO, 400 MHz) 1.45 (3H, s), 1.50 (3H, s), 1.92 (3H, s), 3.19 (2H, brs), 3.36 (3H, brs), 4.43 (2H, q), 4.61 (2H, s), 5.34 (1H, s), 6.10 (1H, s), 7.73 (1H, d), 7.82 (1H, d), 7.91 (1H, s), 9.44 (1H, s). | 3.74 |
| I-3 | 572 | (d6-DMSO, 400 MHz) 1.05-1.15 (1H, m), 1.20-1.40 (4H, m), 1.55-1.65 (1H, m), 1.70-1.85 (4H, m), 2.05-2.10 (3H, m), 3.00-3.25 (5H, m), 3.45-3.55 (2H, m), 3.95-4.00 (3H, s), 4.10-4.20 (2H, m), 5.20-5.30 (1H, s), 6.05-6.25 (1H, br s), 7.50-7.55 (1H, d), 7.85-7.90 (1H, d), 8.10 (1H, s), 9.30-9.50 (2H, m) | 3.83 |
| I-4 | 516 | (d6-DMSO, 400 MHz) 0.750-1.00 (4H, m), 1.60-1.80 (3H, s), 2.85-2.95 (1H, m), 3.00-3.30 (4H, m), 3.40-3.60 (2H, m), 4.00-4.10 (2H, s), 5.10-5.20 (1H, s), 6.00-6.20 (1H, br s), 7.55-7.60 (1H, d), 7.80-7.85 (1H, d), 7.90-8.00 (1H, s), 9.15-9.35 (2H, m). | 3.56 |
| I-5 | 544.43 | (d6-DMSO, 400 MHz) 0.86 (2 H, m), 0.96 (2 H, m), 1.76 (3 H, br s), 2.89 (1 H, m), 3.29-3.10 (4 H, m), 3.85 (3 H, s), 4.25-3.85 (4 H, masked signal), 4.24 (2 H, q), 5.25 (1 H, br s), 6.08 (1 H, br s), 7.42 (1 H, dd), 7.72 (1H, d), 7.87 (1 H, d), 9.38 (1 H, s). | 3.51 |
| I-6 | 525 | (d6-DMSO, 400 MHz) 1.19 (3H, brs), 1.21 (3H, brs), 1.60 (3H, brs), 2.48 (3H, s), 2.98 (2H, brs), 3.15 (3H, brs), 3.85 (2H, brs), 5.11 (1H, s), 5.91 (1H, brs), 7.39 (1H, d), 7.51 (1H, dd), 7.87 (1H, s), 8.17 (1H, d), 9.23 (1H, s), 9.41 (1H, brs). | 3.82 |
| I-7 | 578.44 | (d6-DMSO, 400 MHz) 1.45 (3 H, s), 1.51 (3 H, s), 1.75 (3 H, br s), 3.85-3.17 (13 H, masked signals), 4.23 (2 H, q), 5.23 (1 H, br s), 6.03 (1 H, br s), 7.42 (1 H, dd), 7.71 (1 H, d), 7.87 (1 H, d), 9.39 (1 H, s). | 3.75 |
| I-8 | 558 | (d6-DMSO, 400 MHz) 1.05-1.18 (1H, m), 1.20-1.40 (4H, m), 1.55-1.70 (3H, m), 1.75-1.85 (2H, m), 2.00-2.10 (3H, m), 3.00-3.30 (5H, m), 3.45-3.50 (2H, m), 4.05-4.10 (2H, m), 5.10-5.20 (1H, s), 6.05-6.15 (1H, br s), 7.55-7.60 (1H, d), 7.80-7.85 (1H, m), 7.95-8.00 (1H, s), 9.35-9.45 (2H, s). | 3.7 |
| I-9 | 558 | (d6-DMSO, 400 MHz) 1.65-1.75 (3H, s), 2.55-2.65 (4H, m), 3.15-3.25 (2H, qd), 3.35-3.40 (4H, m), 5.15-5.20 (1H, s), 5.95-6.05 (1H, br s), 7.55-7.60 (1H, d), 7.75-7.80 (1H, d), 7.95-8.00 (1H, s), 9.20-9.25 (1H, s). | 3.65 |
| I-10 | 530 | (d6-DMSO, 400 MHz) 0.750-1.00 (4H, m), 1.75-1.85 (3H, s), 2.85-2.95 (1H, m), 3.05-3.35 (4H, m), 3.45-3.60 (2H, m), 3.95-4.00 (3H, s), 4.10-4.25 (2H, m), 5.20-5.30 (1H, s), 6.05-6.25 (1H, br s), 7.55-7.60 (1H, d), 7.80-7.90 (1H, d), 8.10 (1H, s), 9.30-9.50 (2H, m). | 3.67 |
| I-11 | 550 | (CD$_3$OD, 400 MHz): 1.67 (3H, s), 1.73 (3H, s), 2.14-2.17 (3H, s), 3.55-3.70 (6H, m), 3.90-4.10 (4H, br s), 5.80 (1H, s), 6.20 (1H, s), 7.70-7.75 (1H, d), 7.80-7.85 (1H, d), 8.52 (1H, s), 8.96 (1H, s). | 385 |
| I-12 | 587.8 | (d6-DMSO, 400 MHz) 1.7-1.85 (6H, m), 2.3-2.4 (2H, m), 2.7 (3H, s), 2.9-3.0 (2H, m), 3.05-3.2 (2H, m), 3.6-3.7 (2H, m), 3.95 (3H, m), 5.35 (1H, brs), 6.05 (1H, brs), 7.6 (1H, d), 7.95 (1H, d), 8.12 (1H, s), 9.45 (1H, brs), 9.7 (1H, vbrs), 10.3 (1H, brs) | 3.24 |
| I-13 | 548.46 | (d6-DMSO, 400 MHz) 1.35-1.50 (2H, m), 1.64-1.90 (6H, m), 2.10-2.18 (4H, m), 2.45-2.54 (6H, m), 2.70-2.84 (5H, m), 3.35 (3H, m), 5.33 (1H, brs), 6.12 (1H, brs), 7.57 (1H, d), 7.71 (1H, d), 8.05 (1H, s), 8.38 (1H, d), 9.25 (1H, s), 11.67 (1H, s). | 3.18 |
| I-14 | 516 | (d6-DMSO, 400 MHz) 0.55-0.60 (2H, m), 0.65-0.70 (2H, m), 1.50-1.60 (3H, s), 2.55-2.65 (1H, m), 2.80-3.10 (4H, m), 3.20-3.35 (2H, m), 3.80-4.00 (2H, m), 5.10-5.15 (1H, s), 5.85-6.00 (1H, s), 7.25-7.30 (1H, d), 7.45-7.50 (1H, d), 8.31 (1H, s), 8.70 (1H, s), 9.15-9.20 (1H, s). | 3.67 |

TABLE 2-continued

| Compound No | M + 1 (obs) | 1H NMR | Rt (mins) |
|---|---|---|---|
| I-15 | 491 | (d6-DMSO, 400 MHz). 80-0.95 (4H, m), 1.75-1.80 (2H, m), 2.00-2.10 (3H, s), 2.65-2.70 (3H, m), 3.05-3.25 (5H, m), 3.40-3.50 (2H, m), 4.10-4.20 (2H, m), 5.30-5.40 (1H, s), 6.05-6.25 (1H, br s), 7.55-7.60 (1H, d), 7.70-7.75 (1H, d), 8.07 (1H, s), 8.37-3.90 (1H, d), 9.40-9.50 (2H, m) | 3.66 |
| I-16 | 478.5 | (CD$_3$OD, 400 MHz): 1.5 (9H, s, tBu), 1.8 (3H, s, CH3), 3.05-3.25 (4H, m, alk), 3.55-3.75 (2H, m, alk), 4.15 (3H, s, CH3), 4.4-4.6 (3H, s, CH3), 5.35 (H, s, ar), 6.0 (H, s, ar), 7.6-7.7 (2H, q, ar), 8.05 (H, s, ar) and 8.1 (H, s, ar). | 3.56 |
| I-17 | 584 | (d6-DMSO, 400 MHz) 1.64 (3H, brs), 1.79-1.91 (2H, m), 2.28-2.33 (2H, m), 2.79 (4H, s), 2.91-3.00 (2H, m), 3.25 (4H, brs), 5.22 (1H, brs), 6.15 (1H, vbrs), 8.05-8.10 (2H, m), 8.23 (1H, d), 8.48 (1H, s), 8.79 (1H, d), 9.50 (1H, s), 9.62 (1H, brs), 10.11 (1H, vbrs), 11.75 (1H, vbrs). NB water peak obscures some signals. | 3.6 |
| I-18 | 478.48 | (CD$_3$OD, 400 MHz): 1.35-1.55 (11H, m, CH3, and tBu), 1.9 (3H, s, CH3), 3.0-3.3 (4H, m, alk), 3.6-3.75 (2H, m, alk), 3.95 (3H, s, CH3), 4.35-4.6 (H, m, alk), 5.4 (H, s, ar), 6.0 (H, brs, ar), 7.55 (H, d, ar), 7.75 (H, d, ar), 7.9 (H, s, ar) and 8.3 (H, s, ar). | 3.37 |
| I-19 | 586.5 | (d6-DMSO, 400 MHz) 1.42-1.10 (5 H, m), 1.63 (1 H, d), 1.76 (3 H, br s), 1.79 (2 H, d), 2.06 (2 H, d), 3.21-3.05 (5 H, m), 3.52 (2 H, d), 4.17 (2 H, d), 4.24 (2 H, q), 5.24 (1 H, br s), 6.06 (1 H, br s), 7.42 (1 H, dd), 7.72 (1 H, d), 7.87 (1 H, d), 9.39 (1 H, s), 9.47 (1 H, br s). | 3.65 |
| I-20 | 545 | (d6-DMSO, 400 MHz) 0.80-0.95 (4H, m), 1.85-1.95 (3H, s), 2.85-2.95 (2H, m), 3.05-3.13 (2H, m), 3.16-3.30 (2H, m), 3.50-3.60 (2H, m), 4.10-4.25 (2H, m), 4.40-4.50 (2H, qd), 4.60-4.65 (2H, s), 5.30-5.40 (1H, s), 6.05-6.25 (1H, br s), 7.70-7.75 (1H, d), 7.80-7.85 (1H, d), 7.90 (1H, s), 9.30-9.50 (2H, m). | 3.62 |
| I-21 | 564 | (d6-DMSO, 400 MHz) 1.45 (3H, s), 1.50 (3H, s), 1.77 (3h, s), 3.16 (2H, brs), 3.32 (2H, brs), 3.51 (3H, brs), 3.96-4.08 (5H, m), 5.25 (1H, s), 6.07 (1H, s), 7.56 (1H, dd), 7.89 (1H, d), 8.12 (1H, s), 9.40 (1H, s). | 3.83 |
| I-22 | 558 | (CD$_3$OD, 400 MHz): 2.10-2.15 (3H, s), 2.60-2.65 (4H, m), 3.05-3.15 (2H, qd), 3.45-3.50 (4H, s), 5.70-5.75 (1H, s), 5.83-5.88 (1H, s), 7.60-7.65 (1H, d), 7.70-7.75 (1H, d), 8.38 (1H, s), 8.84 (1H, s). | 3.75 |
| I-23 | 533 | (d6-DMSO, 400 MHz) 1.45-1.55 (3H, m), 2.40-2.45 (4H, m), 2.50 (3H, s), 2.95-3.05 (2H, m), 3.10-3.15 (4H, m), 5.10 (1H, s), 5.80-5.90 (1H, br s), 7.35-7.40 (1H, d), 7.50-7.55 (1H, d), 7.80 (1H, s), 8.12-8.17 (1H, d), 9.40-9.05 (2H, m) | 3.75 |
| I-24 | 587 | (d6-DMSO, 400 MHz) 1.85-1.95 (3H, s), 2.60-2.70 (4H, m), 3.15-3.25 (2H, qd), 3.35-3.40 (4H, m), 4.40-4.45 (2H, qd), 4.60-4.65 (2H, s) 5.30-5.40 (1H, s), 6.05-6.25 (1H, br s), 7.70-7.75 (1H, d), 7.80-7.85 (1H, d), 7.90 (1H, s), 9.30 (1H, s). | 3.67 |
| I-25 | 587 | (d6-DMSO, 400 MHz) 1.05-1.15 (1H, m), 1.20-1.40 (4H, m), 1.55-1.65 (1H, m), 1.80-1.95 (5H, m), 2.05-2.10 (2H, m), 3.00-3.25 (5H, m), 3.50-3.55 (2H, m), 4.10-4.20 (2H, m), 4.40-4.50 (2H, m), 4.60-4.65 (2H, s), 5.30-5.40 (1H, s), 6.05-6.25 (1H, br s), 7.70-7.75 (1H, d), 7.80-7.85 (1H, d), 7.90 (1H, s), 9.30-9.50 (2H, m) | 3.78 |

Example 8

Aurora-2 (Aurora A) Inhibition Assay

Compounds were screened for their ability to inhibit Aurora-2 using a standard coupled enzyme assay (Fox et al., Protein Sci., (1998) 7, 2249). Assays were carried out in a mixture of 100 mM Hepes (pH7.5), 10 mM MgCl$_2$, 1 mM DTT, 25 mM NaCl, 2.5 mM phosphoenolpyruvate, 300 μM NADH, 30 μg/ml pyruvate kinase and 10 μg/ml lactate dehydrogenase. Final substrate concentrations in the assay were 400 μM ATP (Sigma Chemicals) and 570 μM peptide (Kemptide, American Peptide, Sunnyvale, Calif.). Assays were carried out at 30° C. and in the presence of 40 nM Aurora-2.

An assay stock buffer solution was prepared containing all of the reagents listed above, with the exception of Aurora-2 and the test compound of interest. 55 μl of the stock solution was placed in a 96 well plate followed by addition of 2 μl of DMSO stock containing serial dilutions of the test compound (typically starting from a final concentration of 7.5 μM). The plate was preincubated for 10 minutes at 30° C. and the reaction initiated by addition of 10 μl of Aurora-2. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Compounds I-2, I-4 to I-7, I-9, I-17, I-20, I-21, and I-24 were found to inhibit Aurora A at ≦1 nM Ki.

Compounds I-10, I-12 to I-15, I-18, I-19, and I-23 were found to inhibit Aurora A at >1 nM and ≦2 nM Ki.

Compounds I-1, I-3, I-8, I-11, I-16, I-22, and I-25 were found to inhibit Aurora A at >2 nM Ki and ≦20 nM Ki.

Example 9

Aurora-1 (Aurora B) Inhibition Assay (Radiometric)

An assay buffer solution was prepared which consisted of 25 mM HEPES (pH 7.5), 10 mM $MgCl_2$, 0.1% BSA and 10% glycerol. A 22 nM Aurora-B solution, also containing 1.7 mM DTT and 1.5 mM Kemptide (LRRASLG), was prepared in assay buffer. To 22 µL of the Aurora-B solution, in a 96-well plate, was added 2 µl of a compound stock solution in DMSO and the mixture allowed to equilibrate for 10 minutes at 25° C. The enzyme reaction was initiated by the addition of 16 µl stock [γ-$^{33}$P]-ATP solution (~20 nCi/µL) prepared in assay buffer, to a final assay concentration of 800 µM. The reaction was stopped after 3 hours by the addition of 16 µL 500 mM phosphoric acid and the levels of $^{33}$P incorporation into the peptide substrate were determined by the following method.

A phosphocellulose 96-well plate (Millipore, Cat no. MAPHNOB50) was pre-treated with 100 µL of a 100 mM phosphoric acid prior to the addition of the enzyme reaction mixture (40 µL). The solution was left to soak on to the phosphocellulose membrane for 30 minutes and the plate subsequently washed four times with 200 µL of a 100 mM phosphoric acid. To each well of the dry plate was added 30 µL of Optiphase 'SuperMix' liquid scintillation cocktail (Perkin Elmer) prior to scintillation counting (1450 Microbeta Liquid Scintillation Counter, Wallac). Levels of non-enzyme catalyzed background radioactivity were determined by adding 16 µL of the 500 mM phosphoric acid to control wells, containing all assay components (which acts to denature the enzyme), prior to the addition of the [γ-$^{33}$P]-ATP solution. Levels of enzyme catalyzed $^{33}$P incorporation were calculated by subtracting mean background counts from those measured at each inhibitor concentration. For each Ki determination 8 data points, typically covering the concentration range 0-10 µM compound, were obtained in duplicate (DMSO stocks were prepared from an initial compound stock of 10 mM with subsequent 1:2.5 serial dilutions). Ki values were calculated from initial rate data by non-linear regression using the Prism software package (Prism 3.0, Graphpad Software, San Diego, Calif.).

Compounds I-12, I-17, I-18, and I-22 were found to inhibit Aurora A at ≦10 nM Ki.

Compounds I-1 to I-5, I-7, I-8, I-10, I-13, I-19, I-20, I-24, and I-25 were found to inhibit Aurora A at >10 nM and ≦20 nM Ki.

Compounds I-6, I-9, I-11, I-14 to I-16, I-21, and I-23 were found to inhibit Aurora A at >20 nM Ki and ≦50 nM Ki.

Example 10

Microsomal Stability Assay

Microsomal stability was monitored by generation of depletion-time profiles in microsomes from a range of species (male CD-1 mouse, male Sprague-Dawley rat, male Beagle dog, male Cynomolgus monkey and pooled mixed gender human). Compound spiking solutions were made up by diluting down the compound stock solution in DMSO (typically 10 mM) to give a solution in acetonitrile (0.5 mM). Compound (to give final concentration of 5 µM) was incubated with a final reaction mixture (1000 µL) consisting of liver microsome protein (1 mg/mL) and a β-nicotinamide adenine dinucleotide phosphate, reduced form (NADPH)-regenerating system (RGS) [consisting of 2 mM β-nicotinamide adenine dinucleotide phosphate (NADP), 20.5 mM isocitric acid, 0.5 U of isocitrate dehydrogenase/mL, 30 mM magnesium chloride, and 0.1 M phosphate buffer (PB) pH 7.4] in the presence of 0.1 M PB (pH 7.4).

The reaction was initiated by the addition (250 µL) of the pre-incubated RGS to the pre-incubated microsome/VRT/PB mixture (pre-incubation in both instances was for 10 minutes at 37° C.). Samples were incubated within Eppendorf vials (1.5 ml) on a heater shaker (DPC Micromix 5 (settings; form 20, amplitude 4) modified to be heated, to 37° C., by two plate heaters fixed to the deck and controlled by a Packard Manual Heater) attached to a Multiprobe II HT Ex automated liquid handler. The liquid handler was programmed (WinPREP software) to sample the microsomal incubation mixture after 0, 2, 10, 30 and 60 minutes of incubation and transfer an aliquot (100 µL) to a stop block (96-well block) containing 100 µL of chilled methanol. The % organic in the stop mixture was optimized for analysis by addition of appropriate volumes of aqueous/organic (typically 100 µL of 50:50 methanol:water).

Prior to analysis the stop block was placed on a shaker (DPC Micromix 5; 10 min, form 20, amplitude 5) to precipitate out proteins. The block was then centrifuged (Jouan GR412; 2000 rpm, 15 min, 4° C.). A sample aliquot (200 µL) was then transferred to an analysis block and the block was centrifuged again (Jouan GR412; 2000 rpm, 5 min, 4° C.) prior to being sent for analysis. Depletion profiles were determined by monitoring the disappearance of VRT by liquid chromatography-tandem mass spectrometry (LC-MS/MS). Samples were injected (20 µL; Agilent 1100 liquid chromatographic system equipped with autosampler) onto an analytical column. Mobile phase consisted of Water+0.05% (v/v) formic acid (A) and methanol+0.05% (v/v) formic acid (B).

Running a gradient method optimized for the compound of interest carried out the compound elution from analytical column. The total run time was 6 minutes with a flow rate of 0.35 mL/min. The entire column effluent entered the electrospray ionization source (positive mode) of a Micromass Quattro LC tandem mass spectrometer between 0.5 and 5.9 min of the run. The mass spectrometry was optimized for the compound of interest. All incubations were conducted in duplicate and results were expressed as % parent remaining at either 30 minutes or 60 minutes relative to 0 minutes sample.

The following compounds were found to have >50% parent remaining after 30 minutes incubation with human liver microsomes: I-1, I-3, I-4, I-8 to I-12, I-14, I-17, and I-21 to I-23.

The following compounds were found to have >50% parent remaining after 60 minutes incubation with human liver microsomes: I-13 and I-17.

Example 11

Analysis of Cell Proliferation and Viability

Compounds were screened for their ability to inhibit cell proliferation and their effects on cell viability using Colo205 cells obtained from ECACC and using the assay shown below.

Colo205 cells were seeded in 96 well plates and serially diluted compound was added to the wells in duplicate. Control groups included untreated cells, the compound diluent (0.1% DMSO alone) and culture medium without cells. The cells were then incubated for 72 or 96 hrs at 37 C in an atmosphere of 5% CO2/95% humidity.

To measure proliferation, 3 h prior to the end of the experiment 0.5 µCi of 3H thymidine was added to each well. Cells were then harvested and the incorporated radioactivity counted on a Wallac microplate beta-counter. Cell viability was assessed using Promega CellTiter 96AQ to measure MTS conversion. Dose response curves were calculated using either Prism 3.0 (GraphPad) or SoftMax Pro 4.3.1 LS (Molecular Devices) software.

The following compounds had IC50 values of <50 nM after 72 hours: I-3, I-5, I-7, I-8, I-12, I-13, I-19, I-20, and I-25.

The following compounds had IC50 values of ≧50 nM and <100 nM after 72 hours: I-1, I-2, I-4, I-10, I-17, and I-24.

The following compounds had IC50 values of ≧100 nM and ≦1 uM nM after 72 hours: I-6, I-9, I-11, I-14, I-15, and I-21 to I-23.

The following compounds had IC50 values of <50 nM after 96 hours: I-3, I-10, I-16, and I-18.

Example 12

Abl Kinase Activity Inhibition Assay and Determination of the Inhibition Constant Ki Compounds were screened for their ability to inhibit N-terminally truncated (Δ27) Abl kinase activity using a standard coupled enzyme system (Fox et al., *Protein Sci.*, 7, pp. 2249 (1998)). Reactions were carried out in a solution containing 100 mM HEPES (pH 7.5), 10 mM $MgCl_2$, 25 mM NaCl, 300 µM NADH, 1 mM DTT and 3% DMSO. Final substrate concentrations in the assay were 110 µM ATP (Sigma Chemicals, St Louis, Mo.) and 70 µM peptide (EAIYAAPFAKKK, American Peptide, Sunnyvale, Calif.). Reactions were carried out at 30° C. and 21 nM Abl kinase. Final concentrations of the components of the coupled enzyme system were 2.5 mM phosphoenolpyruvate, 200 µM NADH, 60 µg/ml pyruvate kinase and 20 µg/ml lactate dehydrogenase.

An assay stock buffer solution was prepared containing all of the reagents listed above with the exception of ATP and the test compound of interest. The assay stock buffer solution (60 µl) was incubated in a 96 well plate with 2 µl of the test compound of interest at final concentrations typically spanning 0.002 µM to 30 µM at 30° C. for 10 min. Typically, a 12 point titration was prepared by serial dilutions (from 1 mM compound stocks) with DMSO of the test compounds in daughter plates. The reaction was initiated by the addition of 5 µl of ATP (final concentration 110 µM). Rates of reaction were obtained using a Molecular Devices Spectramax plate reader (Sunnyvale, Calif.) over 10 min at 30° C. The Ki values were determined from the residual rate data as a function of inhibitor concentration using nonlinear regression (Prism 3.0, Graphpad Software, San Diego, Calif.).

Compounds I-13, I-16, I-17, and I-18 were found to inhibit Abl kinase at a Ki value of <25 nM.

Example 13

Mutant Abl Kinase (T315I) Activity Inhibition Assay and Determination of the Inhibition Constant IC50

Compounds were screened for their ability to inhibit the T315I mutant form of human Abl at Upstate Cell Signaling Solutions (Dundee, UK). In a final reaction volume of 25 µl, the T315I mutant of human Abl (5-10 mU) was incubated with 8 mM MOPS pH 7.0, 0.2 mM EDTA, 50 µM EAIYAAP-FAKKK, 10 mM Mg Acetate, [γ-$^{33}$P-ATP] (specific activity approx. 500 cpm/µmol, 10 mM final assay concentration) and the test compound of interest at final concentrations over the range 0-4 µnM. The reaction was initiated by the addition of the MgATP mix. After incubation for 40 minutes at room temperature, the reaction was stopped by the addition of 5 µl of a 3% phosphoric acid solution. 10 µl of the reaction was then spotted onto a P30 filtermat and washed three times for 5 minutes in 75 mM phosphoric acid and once in methanol prior to drying and scintillation counting. Inhibition IC50 values were determined from non-linear regression analysis of the residual enzyme activities as a function of inhibitor concentration (Prism 3.0, Graphpad Software, San Diego, Calif.).

Compound I-17 was found to inhibit Abl kinase at a Ki value of <25 nM.

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:
1. A compound of formula I:

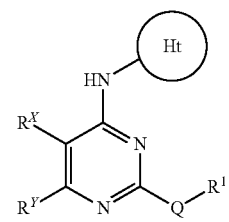

or a pharmaceutically acceptable salt thereof, wherein:
Ht is

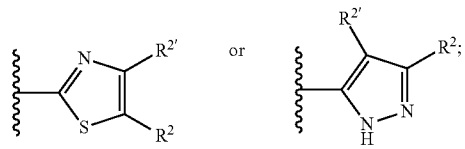

$R^2$ is H, $C_{1-3}$ alkyl, or cyclopropyl;
$R^{2'}$ is H;
Q is —O—, —S—, or —C(R')$_2$—;
R' is H or C1-3alkyl; or
two occurrences of R', taken together with atom to which they are joined, form a 3-5 membered cycloalkyl ring;
$R^X$ is H or F;
$R^Y$ is

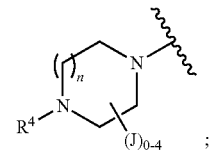

each J is independently F or $C_{1-6}$alkyl;
n is 1 or 2;
$R^4$ is H, $C_{1-6}$alkyl, $C_{3-8}$ cycloaliphatic, or a 4-8 membered heterocyclyl containing 1-2 heteroatoms selected from O, N, or S; wherein said alkyl, cycloaliphatic or heterocyclyl is optionally and independently substituted with 0-6 occurrences of $C_{1-6}$alkyl, —O—($C_{1-6}$alkyl), $NH_2$, OH, =O, halo, CN, or $NO_2$;

$R^1$ is an 8-12 membered bicyclic heteroaryl ring containing 1-5 heteroatoms selected from O, N, and S and optionally substituted with 0-4 $J^D$;

each $J^D$ is independently $C_{1-6}$alkyl, —O—($C_{1-6}$alkyl), halo, or oxo wherein each $C_{1-6}$alkyl is optionally substituted with 0-6 fluoro.

2. The compound of claim 1, wherein Q is —S—.

3. The compound of claim 2, wherein Ht is

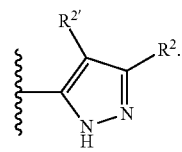

4. The compound of claim 3, wherein $R^2$ is $C_{1-3}$ alkyl or cyclopropyl.

5. The compound of claim 4, wherein $R^{2'}$ is H.

6. The compound of claim 5, wherein Rx is H.

7. The compound of any one of claims 1-6, wherein n is 1.

8. The compound of any one of claims 1-6, wherein n is 2.

9. The compound of claim 6, wherein $R^4$ is H, $C_{1-6}$alkyl, $C_{3-8}$ cycloaliphatic, or a 4-8 membered heterocyclyl containing 1-2 heteroatoms selected from O or N; wherein said alkyl, cycloaliphatic or heterocyclyl is optionally and independently substituted with 0-6 occurrences of $C_{1-6}$alkyl, —O—($C_{1-6}$alkyl), $NH_2$, OH, =O, halo, CN, or $NO_2$.

10. The compound of claim 9, wherein $R^4$ is $C_{1-6}$alkyl, $C_{3-8}$ cycloaliphatic, or a 4-8 membered heterocyclyl containing 1-2 heteroatoms selected from O or N; wherein said alkyl, cycloaliphatic or heterocyclyl is optionally and independently substituted with 0-6 occurrences of $C_{1-6}$alkyl, —O—($C_{1-6}$alkyl), $NH_2$, OH, =O, halo, CN, or $NO_2$.

11. The compound of claim 10, wherein $R^4$ is a 4-8 membered heterocyclyl containing 1-2 heteroatoms selected from O or N.

12. The compound of claim 10, wherein $R^4$ is a 5-6 membered heterocyclyl containing 1-2 heteroatoms selected from O or N.

13. The compound of claim 10, wherein $R^4$ is $C_{1-6}$alkyl.

14. The compound of claim 10, wherein $R^4$ is $C_{3-6}$ cycloalkyl.

15. The compound of claim 10, wherein $R^1$ is an 8-12 membered bicyclic heteroaryl containing 1-5 heteroatoms selected from O, N, and S and optionally substituted with 0-4 $J^D$.

16. The compound of claim 15, wherein $R^1$ is a 6:6 ring system.

17. The compound of claim 16, wherein $R^1$ is quinoline.

18. The compound of claim 15, wherein $R^1$ is a 6:5 ring system.

19. The compound of claim 18, wherein said 6:5 ring system contains 2 nitrogen atoms.

20. The compound of claim 19, wherein $R^1$ is a benzimidazole, indazole, or imidazopyridine ring.

21. The compound of claim 20, wherein $R^1$ is a benzimidazole ring.

22. The compound of claim 1 selected from the following:

I-1

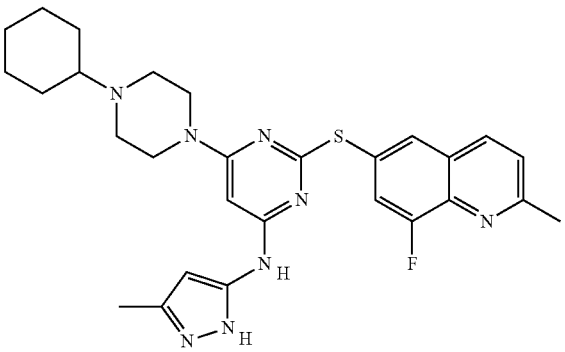

I-2

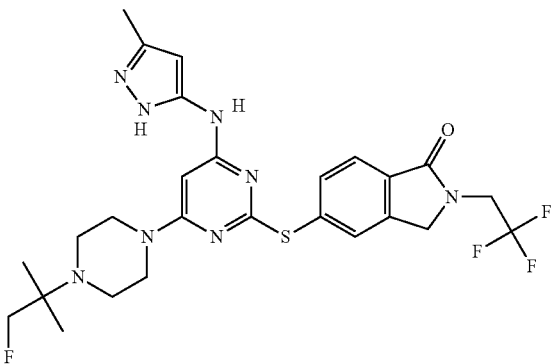

I-3

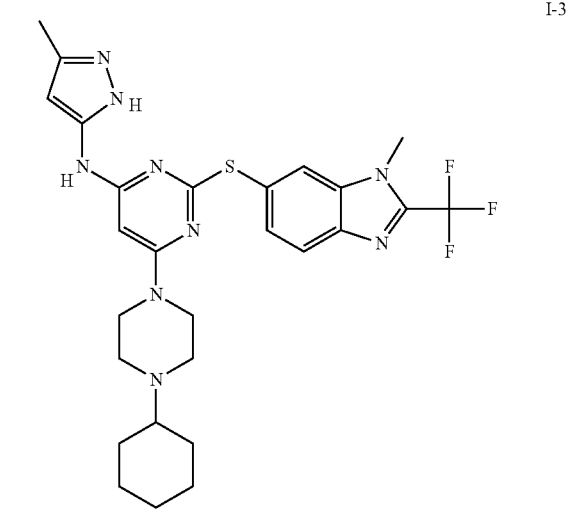

I-4
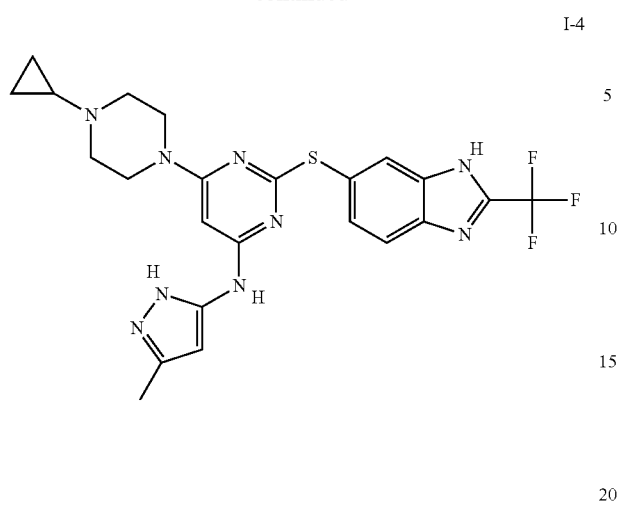
I-7
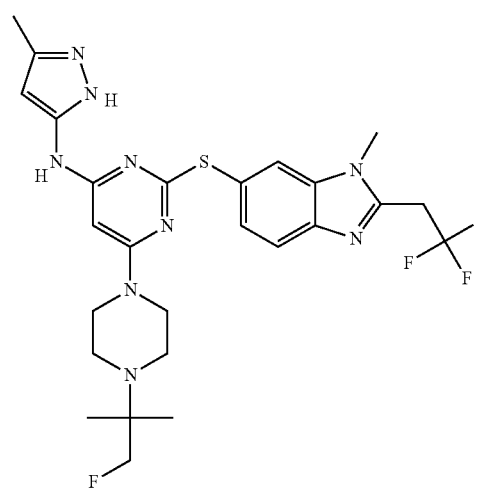
I-5
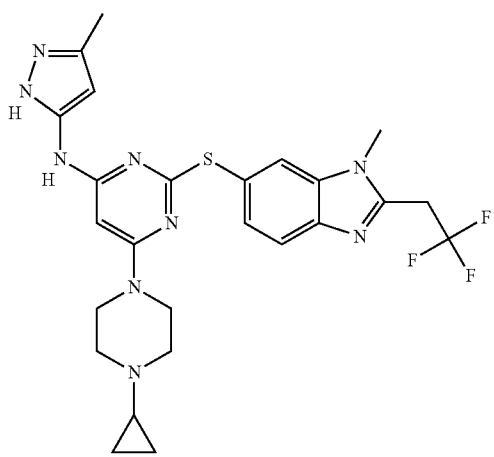
I-8
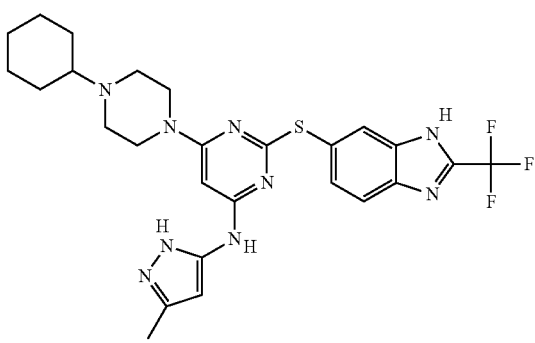
I-6
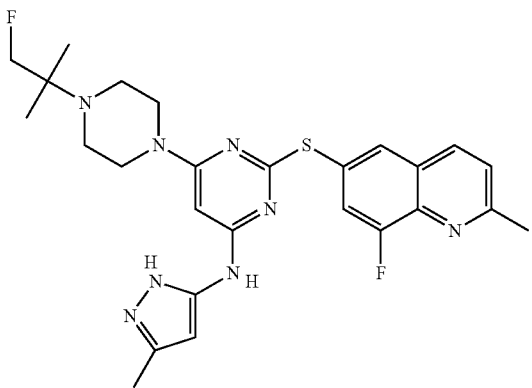
I-9
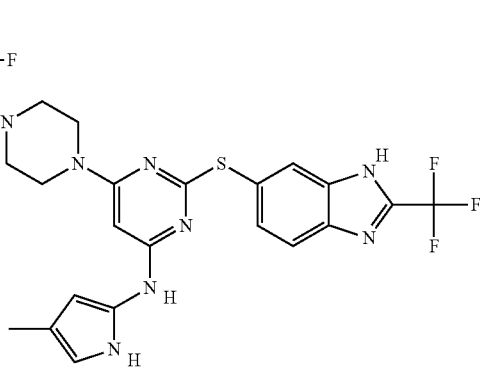

-continued
I-10
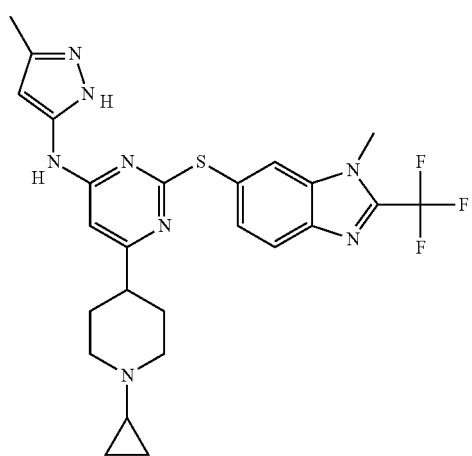
I-11
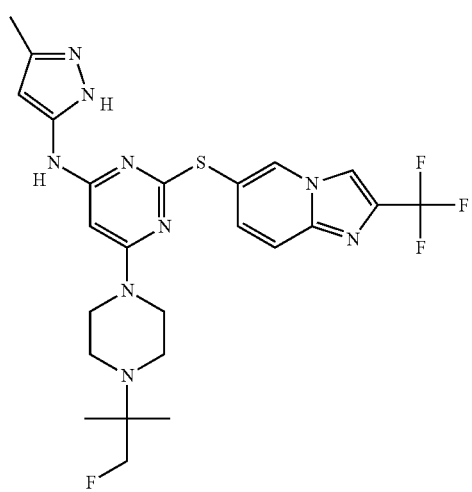
I-12
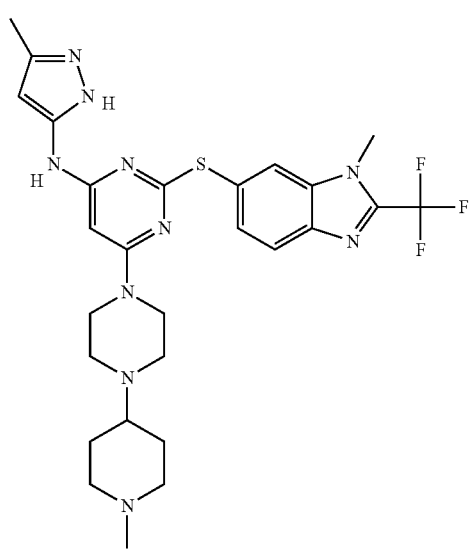
-continued
I-13
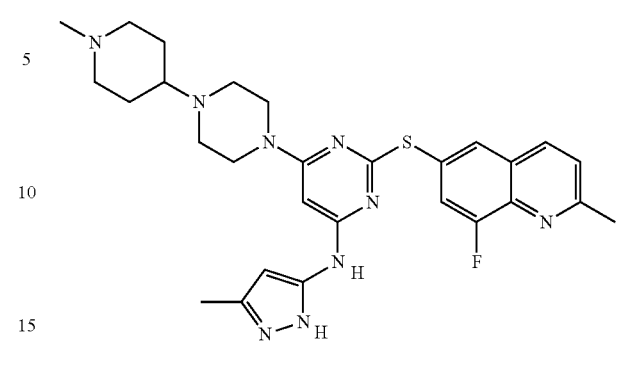
I-14
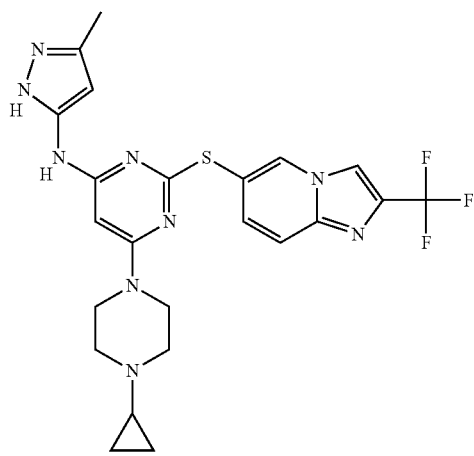
I-15
I-16
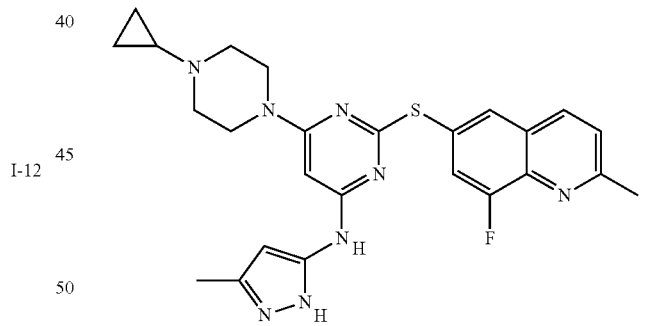

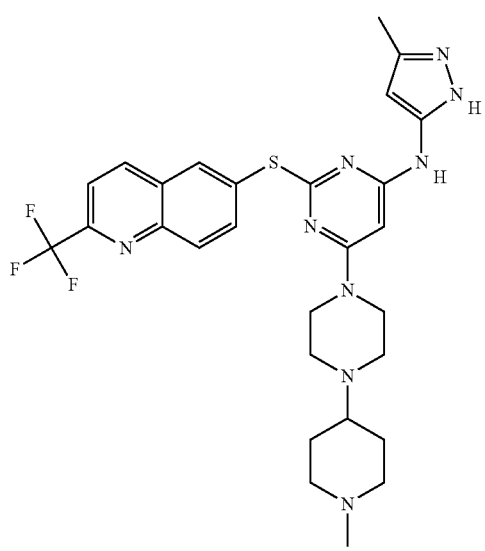
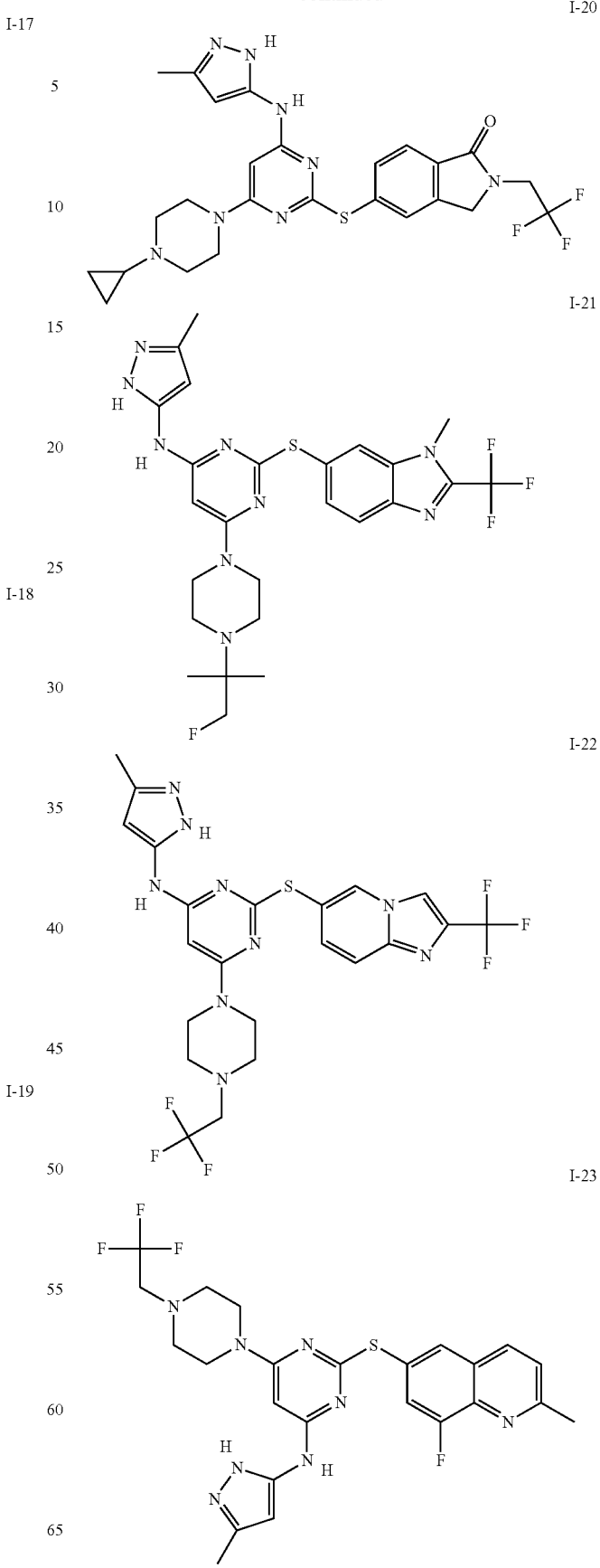

I-24
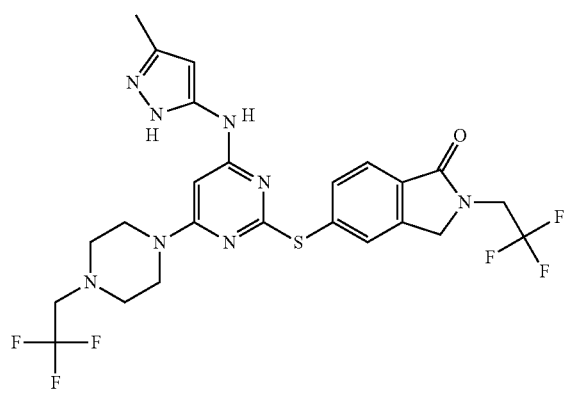
I-25
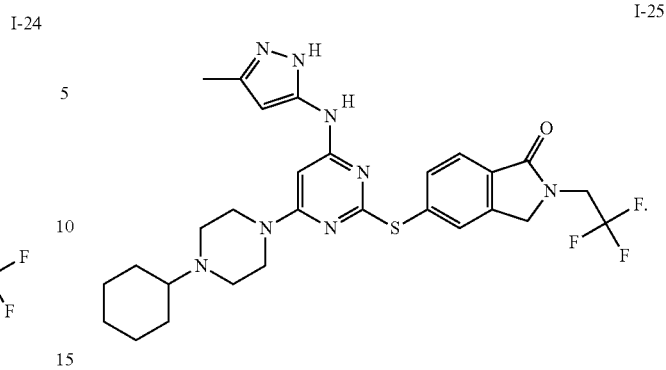
23. A pharmaceutical composition comprising a compound of any one of claims 1-22 and a pharmaceutically acceptable carrier.
* * * * *